United States Patent
Murase et al.

[11] Patent Number: 5,914,449
[45] Date of Patent: Jun. 22, 1999

[54] METHOD FOR INCREASING STORAGE LIPID CONTENT IN PLANT SEED

[75] Inventors: Makoto Murase; Junko Murase, both of Yokohama; Mari Iwabuchi, Akita; Takahiko Hayakawa; Jun Imamura, both of Yokohama, all of Japan

[73] Assignees: Mitsubishi Corporation; Mitsubishi Chemical Corporation, both of Tokyo, Japan

[21] Appl. No.: 08/791,849

[22] Filed: Jan. 30, 1997

[30] Foreign Application Priority Data

Feb. 1, 1996 [JP] Japan .................... 8-016590

[51] Int. Cl.[6] .............. A01H 5/00; C12N 5/14; C12N 15/00

[52] U.S. Cl. .............. 800/281; 800/286; 800/287; 800/306; 800/312; 800/322; 800/298

[58] Field of Search .................... 800/205, 250, 800/281, 286, 287, 306, 312, 322, 298; 536/23.6

[56] References Cited

U.S. PATENT DOCUMENTS 5,530,192  6/1996  Murase et al. .................... 800/205

FOREIGN PATENT DOCUMENTS 0 620 281 A2  10/1994  European Pat. Off. .
94/29467      12/1994  WIPO .

OTHER PUBLICATIONS

Burton et al. Crop Science 21:31–34, Feb. 1981.
Finnegan et al. Bio/Technology 12:883–888, Sep. 1994.
Smith et al. Crop Science 29:349–353, Mar. 1989.
Database WPI, Section Ch, Week 9506, Derwent Publications Ltd., London, GB; Class C06, AN 95–040320 XP002058807 & JP 06 319 567 A (Mitsui Gyosai Shokubutsu Bio Kenkyusho), Nov. 22, 1994 * abstract*.

*Primary Examiner*—Elizabeth Kemmerer
*Attorney, Agent, or Firm*—Wenderoth, Lind & Ponack, L.L.P.

[57] ABSTRACT

In order to obtain a crop which provides an increased storage lipid content in its seed, the activity of cytosolic pyruvate kinase of a seed is substantially lowered as compared with the endogenous activity of pyruvate kinase in the plant seed. Preferably, the activity of phosphoenolpyruvate carboxylase is substantially lowered as compared with the endogenous activity of phosphoenolpyruvate carboxylase in the seed. Thus the storage lipid content in the plant seed is increased.

13 Claims, 1 Drawing Sheet

METHOD FOR INCREASING STORAGE LIPID CONTENT IN PLANT SEED

BACKGROUND OF THE INVENTION

1. Field of the Invention

The present invention relates to a method for increasing a storage lipid content in a plant seed. The present invention also relates to a plant with an increased storage lipid content in its seeds. Further, the present invention relates to seeds with an increased storage lipid content.

2. Description of the Related Art

Plants belonging to the genus Brassica, which bear seeds containing lipid in an amount of about 40% by weight, are now cultivated as oil plants at many places in the world. As for rapeseed, a variety has been created by means of a cross breeding method in order to decrease the content of harmful substances such as erucic acid and glucosinolate. Until the present, a lipid content of about 40% based on the weight of seed has been achieved by means of cross breeding. However, the amount of vegetable oil consumption is increasing as compared with animal oil because people are interested in healthy life. Therefore, achievement of a high lipid content is ranked to be a first target in the breeding for rapeseed, and it is desired to further increase the lipid content.

However, the following problems have arisen. Namely, there is no variety to be used as a genetic source having a high lipid content for mating. The conventional breeding involves an extremely laborious and time-consuming process in which a species having an objective character is selected from random variations, which is non-oriented mutation so that a pure line is established. Therefore, the increase in lipid content achieved by the breeding based on mating has a certain limit in the present circumstances.

On the contrary, the process to create a recombinant plant based on the use of gene manipulation can provide a breeding method associated with extremely high orientation, because only a gene concerning an objective character is dealt with to make artificial modification and introduction. For example, the lipid composition in a plant has been modified by introducing antisense DNA, i.e., a DNA sequence coding for antisense RNA (antisense oligonucleotide). Those known for such modification include, for example, the fact that the oleic acid content is decreased and the stearic acid content is increased by introducing, into rapeseed, an antisense gene of stearate desaturase (*Proc. National Acad. Sci. USA*, 89, 2624, 1992).

Storage compounds in seeds are different in quantitative ratio depending on plants which accumulate the storage compounds. However, the storage compounds principally include lipid, protein, and carbohydrate. It is known that these substances are produced and accumulated in an approximately simultaneous period during the development period of seed, i.e., cell division and cell elongation stage, and their biosynthetic pathways are closely correlated with each other. Namely, an assimilated product produced by photosynthesis is used as a starting material to proceed biosynthesis of the respective substances. Lipid, protein, and carbohydrate are synthesized and accumulated as final products. Pyruvic acid is one of intermediate products of the biosynthesis of the storage compounds in seed. Pyruvic acid can be a substrate for synthesizing lipid, protein, and carbohydrate. In the case of rapeseed, lipid and protein are principally accumulated as storage compounds, and carbohydrate is scarcely accumulated. Accordingly, lipid synthesis is possibly affected if any one of reactions in the biosynthesis pathway for storage protein in seed is inhibited. Those conceived as a method to achieve such a situation include inhibition of biosynthesis of storage protein in seed based on the use of an antisense gene directed to pyruvate kinase which synthesizes pyruvic acid and ATP from phosphoenolpyruvate and ADP, and an antisense gene directed to phosphoenolpyruvate carboxylase which uses, as a substrate, phosphoenolpyruvate to serve as a substrate for pyruvate kinase.

In all eukaryotes, pyruvate kinase is found within the cytosol. However, in plants, pyruvate kinase is located also in plastids. These two types of pyruvate kinase differ significantly in their molecular and kinetic characteristics and are immunologically unrelated proteins. Among them, those determined and reported for the former include a complete nucleotide sequence of cDNA of castor oil seed (*Plant Physiol.*, 96, 1238–1288, 1991) and a nucleotide sequence of a cDNA of a tobacco cDNA (*Plant Mol. Biol.*, 27 (1) 79–89, 1995). Those determined and reported for the latter include a complete nucleotide sequence of potato cDNA and an amino acid sequence for castor pyruvate kinase (*Plant Mol. Biol.*, 15, pp. 665–669, 1990), a nucleotide sequence of soybean cDNA (*Plant Physiol.*, 102, 1345, 1993; it has been registered in Genbank under a number of L08632), and a part of a nucleotide sequence for rice pyruvate kinase (EMBL OSAD 11727). However, the relation between the genes and distribution of storage compounds has not been clarified. In addition, in the case of the use of transformation based on the antisense method, homology of the sequence is especially important. Accordingly, it is desirable to use a gene obtained from an objective to be utilized. It has been desired to isolate a gene of pyruvate kinase originating from an oil plant.

SUMMARY OF THE INVENTION

As a result of repeated investigations in order to increase the storage lipid content in seed, the present inventors have noticed that lipid and protein are principally biosynthesized and accumulated from assimilated products by photosynthesis in plants which accumulate storage protein and storage lipid in embryo, such as rape seed, soybean, sunflower, and sesame. The present inventors have found that the amount of the assimilated product to be used for the synthesis of storage protein is decreased, and consequently the synthesis of lipid is apparently enhanced by inhibiting any of reactions in the amino acid biosynthesis pathway included in the biosynthesis pathways for the storage compounds in seed, especially effectively by inhibiting early reactions included in the diverse amino acid biosynthesis pathway. Thus the present invention has been completed.

Namely, the gist of the present invention lies in a method for increasing a storage lipid content in a seed of a plant, comprising the step of substantially lowering a value of activity of cytosolic pyruvate kinase in the seed of the plant as compared with an activity of endogenous cytosolic pyruvate kinase in the seed of the plant.

In another aspect, the present invention lies in a method for the foregoing plant, further comprising the step of substantially lowering a value of activity of phosphoenolpyruvate carboxylase as compared with an activity of the endogenous phosphoenolpyruvate carboxylase in the seed of the plant.

In still another aspect, the present invention lies in a plant obtained by the foregoing method, which provides an increased storage lipid content in its seed.

In still another aspect, the present invention lies in a seed of a plant obtained by the foregoing method, which provides an increased storage lipid content in the seed.

The plant includes plants which accumulate storage compounds in embryo thereof. More specifically, the plant includes oilseed plants such as rapeseed, soybean, sunflower, and sesame.

As for the method of the present invention, the means for lowering the activity of cytosolic pyruvate kinase includes introduction of a DNA sequence coding for pyruvate kinase or a part thereof in a form to suppress expression of cytosolic pyruvate kinase in seed cell, into the objective plant. The means for introducing, into the objective plant, the DNA sequence coding for pyruvate kinase or the part thereof in the form to suppress expression of cytosolic pyruvate kinase in the seed cell includes an antisense method, a co-suppression method, a ribozyme method, and a gene targeting method.

The DNA sequence coding for pyruvate kinase specifically includes cytosolic pyruvate kinase genes of rapeseed, castor bean, potato, soybean and rice, pyruvate kinase genes of rat and yeast, and the part thereof. The DNA sequence coding for pyruvate kinase specifically exemplified by the following (a) and (b):

(a) a sequence defined in any one of SEQ ID NOs:1 and SEQ ID NOs: 11 to 15 in Sequence Listing;

(b) DNA hybridizable under a physiological condition with DNA having the sequence as defined in (a) or RNA having a sequence homologous thereto, and a part thereof.

The present invention will be explained in detail below.

The plant used in the present invention may be any one provided that the plant which synthesizes and accumulates storage protein and storage lipid almost simultaneously as storage compounds of seed in its embryo. Specifically, the plant includes oil plants such as rapeseed, soybean, sunflower, and sesame. The plant is preferably exemplified by rapeseed.

The cytosolic pyruvate kinase of plant seed can be extracted and measured for its activity in accordance with, for example, a method described in *Plant Physiol.*, 86, 1064–1069 (1988) as mentioned in Example described later on. The extraction and the measurement of activity can be appropriately modified in conformity with the species of the objective plant, the part of the objective plant, and the growth period of the objective plant. In the present invention, the value of the activity of the cytosolic pyruvate kinase of the objective plant seed is measured in accordance with the method as described above. The activity is substantially lowered as compared with an endogenous activity in the plant previously measured in accordance with the method as described above. Thus the storage lipid content in the seed of the plant can be increased.

The method for lowering the activity of pyruvate kinase includes, for example, a method for introducing, into the objective plant, all or a part of the DNA sequence coding for pyruvate kinase in a form to suppress expression of pyruvate kinase in the seed cell, for example, in a form to suppress transcription and/or translation of the gene. Such a method includes, for example, an antisense method, a co-suppression method, a ribozyme method, and a gene targeting method as described in detail later on.

Those already known as the DNA sequence coding for pyruvate kinase is exemplified by cytosolic pyruvate kinase genes such as a gene deduced from an amino acid sequence of enzyme of castor bean and a gene of potato (SEQ ID NO: 11), both of which are described in *Plant Mol. Biol.*, 15, 665–669 (1990), a gene of soybean (SEQ ID NO: 12 in Sequence Listing, refer to *Plant Physiol.*, 102, 1345 (1993)) registered in Genbank under a number of L08632, and a gene of rice plant (SEQ ID NO: 13 in Sequence Listing, registered in EMBL under a number of OSAD 11727, a pyruvate kinase gene of rat (SEQ ID NO: 14 in Sequence Listing) described in *FEBS Lett.*, 195, 97–100 (1986), and a pyruvate kinase gene of yeast (SEQ ID NO: 15 in Sequence Listing) described in *J.B.C.*, 258, 2193–2201 (1983). DNA sequences coding for pyruvate kinase other than those known can be isolated from mRNA's of various plants in accordance with the PCR method by using primers prepared on the basis of the nucleotide sequence of the known gene coding for pyruvate kinase as described above. For example, when a gene coding for cytosolic pyruvate kinase of rapeseed is isolated, mRNA is extracted, for example, from developing seed of *B. napus* cv. *Westar* in accordance with the method described in "Molecular Cloning", and cDNA is synthesized by using the extracted mRNA as a template. The obtained DNA is used as a template, and primers are selected and designed from portions having high homology among the gene sequences on the basis of the known gene sequences so that amplification is performed in accordance with the PCR method.

In the process to arrive at completion of the present invention, the gene was amplified by the PCR method twice while changing primers in order to certainly amplify the target DNA region. However, the PCR method may be performed only once. The PCR method (Saiki, *Science*, 239, pp. 487–491, 1988) is a method for amplifying a target DNA region by repeating a series of steps comprising thermal denaturation of a template, annealing between primers and the template, and elongation with heat-resistant polymerase. Especially in the present invention, it is desirable to repeat a series of steps 20 to 40 times to amplify complementary strand DNA, the series of steps comprising thermally denaturating the template DNA and the primers at 94° C. for about 0 to 20 seconds to achieve dissociation into single strands of (+) strand and (−) strand, performing annealing with the primers at 40 to 50° C. for 15 to 30 seconds, and then synthesizing DNA with heat-resistant polymerase (72° C. for about 1 minute). The amplified DNA region may be confirmed, for example, as follows. Namely, the obtained DNA is cloned into pBluescriptII phagemid vectors produced by STRATAGENE, followed by sequencing by using "ABI 373A Sequencer" in accordance with its protocol. It is assumed that the nucleotide sequence described in SEQ ID NO: 1 covers about 30% of a transcription region, according to comparison with other reported nucleotide sequences of pyruvate kinase.

Those usable as the DNA sequence coding for pyruvate kinase to be used in the present invention include entire of the natural gene coding for pyruvate kinase as described above, preferably its coding region, and a part of thereof prepared properly according to a plant cell which is to be introduced the DNA sequence. Further, even DNA sequences having, for example, substitution, deletion, insertion, and transposition in the natural type gene sequence described above may be used as the DNA sequence coding for pyruvate kinase to be used in the present invention, provided that the DNA sequences can hybridize with a cytosolic pyruvate kinase gene in the plant cell or a transcription product thereof under a physiological condition, i.e., under a condition equivalent to that in the plant cell to suppress transcription and/or translation of the cytosolic pyruvate kinase gene. Moreover, the DNA sequence coding for pyruvate kinase to be used in the present invention may originate from cDNA or from genomic DNA containing intron.

A procedure to use the antisense method will be specifically described below. In the antisense method, DNA (antisense DNA), which codes for a sequence homologous to a (−) strand of a target gene, i.e., RNA having a sequence complementary to a sequence of mRNA or a part thereof (antisense RNA), is introduced into cell and expressed therein. In this method, a hybrid between the antisense RNA and mRNA is formed to suppress transcription and/or translation. Therefore, the inhibiting efficiency increases as the homology between mRNA and the nucleotide sequence of the antisense RNA becomes high.

The plant has two types of pyruvate kinases, i.e., the cytosolic and the plastidic pyruvate kinase. It is suggested that a common precursor biosynthesized in cytoplasm is then distributed for amino acid synthesis caused in cytoplasm and for fatty acid synthesis caused in chloroplast. Accordingly, the pathway destined for chloroplast is possibly facilitated by inhibiting any of the amino acid biosynthesis pathways for allowing the substrate to flow into the TCA cycle operated in cytoplasm. Of the two types of pyruvate kinases, it is assumed that the cytosolic pyruvate kinase participates in the distribution to arrive at the protein synthesis in cytoplasm. Therefore, it is preferred to use antisense DNA of the cytosolic pyruvate kinase gene. The cytosolic pyruvate kinase may be hereinafter referred to as simply "pyruvate kinase".

Sequences of pyruvate kinase genes are highly homologous to be not less than 65% among plant species for which the sequences of cDNAs are known for their entire lengths. Among them, the region coding for pyruvate kinase protein has high homology of 70%.

According to analysis for the secondary structure assumed to participate in stability and completion of transcription of transcribed antisense RNA, it is preferred to avoid, as less as possible, a sequence which may form a hairpin structure at a probability of not less than 75%. Based on consideration for the foregoing conditions, a preferred embodiment of the present invention uses, as the antisense DNA, a sequence of rapeseed corresponding to a portion of 345 to 898 bp of a published sequence of potato. Other than this sequence, sequences which satisfy the foregoing conditions can be also used for the present invention.

In general, in order to introduce the DNA sequence coding for pyruvate kinase into the plant cell, a recombinant vector obtained by inserting the DNA sequence into a vector is used. Those usable as the vector in the present invention include vectors which are generally used for transformation for plant cells, depending on methods for introduction into plant cells. For example, plasmids of the plan series are exemplified for the Agrobacterium mediated transformation. Plasmids which are replicable in *Escherichia coli* such as pUC series, pBR322 and those derivatives are exemplified for the electroporation method. The construction of the recombinant vector varies depending on the procedure to stop expression of pyruvate kinase. However, in order to decrease an amount of pyruvate kinase or amounts of both pyruvate kinase and phosphoenolpyruvate carboxylase, and efficiently increase the storage lipid content in seed, it is preferred to use a seed-specific expression promoter. In the case of the use of the antisense method, for example, such a recombinant vector is obtained by introducing the DNA sequence (antisense DNA) coding for antisense RNA for mRNA of pyruvate kinase into a position downstream from the promoter to be expressed seed-specifically.

The seed-specific expression promoter specifically includes, for example, promoters for genes of napin (*Plant Mol. Biol.*, 26, pp. 1115–1124, 1994; *Eur. J. Biochem.*, 227, pp. 316–321, 1995), cruciferin (*Plant Cell Rep.*, 14, pp. 123–130, 1994), phaseolin (*Plant Cell*, 1, pp. 839–853, 1989), legumin (*Mol. Gen. Genet.*, 215, pp. 326–331, 1989; *Mol. Gen. Genet.*, 225, pp. 148–157, 1991), glutenin (*Plant Cell*, 1, pp. 569–578, 1989; *EMBO J.*, 6, pp. 3559–3564, 1987), helianthinin (*Mol. Gen. Genet.*, 222, pp. 49–57, 1990), glutelin (*Plant Mol. Biol.*, 16, pp. 49–58, 1991), and zein (*EMBO J.*, 7, pp. 1249–1255, 1988). However, other promoters having seed-specific expression properties may be used.

Further, in order to efficiently terminate transcription of the gene and stabilize produced RNA, a terminator is used in the case of plant. Specifically, a terminator of a nopaline synthase gene, NOS, is exemplified (pBI221, Jefferson, *EMBO J.*, 6, 3901–3907, 1987). However, other ones which function as a terminator in plant cell may be used.

The form to suppress transcription and/or translation of the gene refers to a DNA sequence for expressing antisense RNA of the target gene (pyruvate kinase gene inherent in cell) in the case of the use of the antisense method, or it refers to a DNA sequence for expressing sense RNA of the target gene in the case of the use of the co-suppression method. The term "suppress" refers to the fact that the transcription and/or translation of the pyruvate kinase gene is inhibited, the value of activity of the cytosolic pyruvate kinase in a seed is made substantially lower than the endogenous acitivity of cytosolic pyruvate kinase in the plant seed, and consequently the storage lipid content in the seed of the plant can be increased. On the foregoing condition, the degree of suppression is not especially specified. Namely, the transcription and/or translation of the target gene may be suppressed completely, or suppressed partially.

The method for introduction into the objective crop in the form to suppress the transcription and/or translation of the gene is not specifically limited, provided that it resides in any one of methods to be generally used, such as the antisense method, the co-suppression method, the ribozyme method, and the gene targeting method.

The co-suppression method is a method in which DNA coding for RNA having a sequence homologous to an entire sequence of mRNA of the target gene or a part thereof (sense RNA) is introduced into cell, and it is expressed therein to suppress transcription and/or translation of the gene. The co-suppression method is also called transwich method. The co-suppression method is exemplified by those applied to petunia (*Plant Cell*, 2, 279–289, 1990), tomato (*Mol. Gen. Genet.*, 224, 477–481, 1990), and tobacco (*Proc. Natl. Acad. Sci. USA*, 88, 1770–1774, 1991).

The ribozyme method is a method in which translation is suppressed by allowing small RNA motif of a hammer head form to digest a specified portion of RNA ("Antisens Research and Applications", Crooke, S. T. and Lebleu B. eds., CRC Press, Inc., pp. 83–96, 1933).

The gene targeting method is a method in which a sequence of an objective genome gene is destroyed to suppress transcription of the gene by means of transposon movable on the genome or by means of homologous recombination ("Homologous Recombination and Gene Silencing in Plants", Paszkowski J. ed., Kluwer Academic Publishers, 1994). In this case, those usable as the DNA sequence to be introduced into cell include, for example, a DNA sequence deficient in a part of a coding region of pyruvate kinase, and a promoter sequence modified not to function.

In the present invention, transformation is preferably performed in accordance with Agrobacterium-mediated transformation (*Bio/technology*, 6, 915–922, 1988; *Bio/technology*, 5, 1201–1204, 1987) and with the electroporation (*Plant Cell Rep.*, 10, 106–110, 1991; *Plant Cell Rep.*, 9, 55–60). However, transformation may be performed in accordance with ordinary transformation such as the particle-acceleration transformation or gene gun method (*Theor. Appl. Genet.*, 79, 337–341, 1990; *Plant Cell Rep.*, 14, 81–86) and the PEG.

In a preferred embodiment of the present invention, a plasmid of the plan type is used when the Agrobacterium-mediated transformation is used as the method for transforming the plant. However, plasmids of other types may be used. It is preferred to introduce, into the plasmid, a so-called selection marker gene effective to select an objective transformant, in addition to the foreign gene to be used for transformation. The selection marker gene is not specifically limited provided that the marker gene is generally used. Specifically, the selection marker gene includes, for example, neomycin phosphotransferase gene, hygromycin phosphotransferase gene, chloramphenicol acetyltransferase gene, and β-glucuronidase gene.

The plasmid, which contains the DNA sequence coding for pyruvate kinase or the part thereof in the form to suppress the transcription and/or translation of the cytosolic pyruvate kinase gene in the cell as described above, and preferably further contains the selection marker gene, is introduced into lower hypocotyl of rapeseed, and a plant body is reproduced. Thus rapeseed, which provides a varied storage lipid content, is created. Lower hypocotyl, which is 10 to 14 days old after germination, can be used for the Agrobacterium-mediated transformation.

Electroporation can be performed in accordance with an ordinary method. Protoplasts to be used for the electroporation can be prepared in accordance with an ordinary method. However, when protoplasts originating from a plant belonging to the genus Brassica are prepared, for example, they can be efficiently obtained in accordance with a method described in Japanese Patent Laid-open No. 4-276069. For example, *B. napus* is transformed by introducing antisense DNA of the pyruvate kinase gene as follows. Namely, protoplasts ($6 \times 10^5$ individuals/ml) originating from *B. napus* cv. *Westar* are suspended in a liquid medium containing 30 to 200 mM potassium chloride, 0 to 50 mM magnesium chloride, and 0.2 to 0.6 M mannitol with the pyruvate kinase antisense DNA expression vector (for example, 40 to 80 µg/ml) prepared as described above and the neomycin phosphotransferase gene (for example, 40 to 80 µg/ml) as the selection gene. Electric pulse is applied to the suspension so that the plasmid is introduced into the protoplasts.

After that, cells are selected in accordance with a method described, for example, in *Plant Molecular Biology*, 26, pp. 1115–1124, 1994 in the case of the Agrobacterium-mediated transformation, or in accordance with a method described, for example, in *Plant Tissue Culture Lett.*, 11, 199–205, 1994 in the case of the electroporation method so that regenerated plants are obtained. Genome DNA is isolated from leaves of the regenerated plants in accordance with, for example, a method described in *Mol. Gen. Gent.*, 211, 27–34, 1988. The genome DNA (300 ng) is subjected to the PCR. Thus it is possible to perform secondary selection for a transformant which incorporates antisense DNA of pyruvate kinase or phosphoenolpyruvate carboxylase. In this procedure, for example, primers to be used are selected from a region ranging from the seed-specific expression promoter described above to the partial sequence of pyruvate kinase. Introduction of the antisense DNA of pyruvate kinase and/or the antisense DNAs of both pyruvate kinase and phosphoenolpyruvate carboxylase is confirmed for transformants which are then acclimatized and conditioned. After that, the transformants are allowed to grow in a greenhouse so that seeds are set after 3 to 6 months.

Existence of the introduced gene can be confirmed by Southern analysis for genomic DNA (Southern, J., *Mol. Biol.*, 98, 503–517, 1975). For example, genome DNA is prepared in accordance with a method described by Wolbot et al. (*Mol. Gen. Gent.*, 211, 27–34, 1988), 10 µg of which is digested with EcoRI in a reaction system (100 µl, produced by Toyobo). A digested product is subjected to ethanol precipitation, subsequently washed with 70% ethanol, and dried. The obtained product is dissolved in redistilled water (10 µl), to which a dye for electrophoresis (2 µl) is added to perform fractionation by means of 0.8% agarose gel electrophoresis (GTG agarose gel produced by FMC Seachem, TBE buffer). The gel is subjected to partial acid degradation and alkali denaturation in accordance with a method described in a manual for Hybond N membrane produced by Amersham to perform blotting to the Hybond N membrane. The membrane is subjected to prehybridization at 42° C. for 1 hour or more (50% formamide, 4×SSCP containing 1% SDS, 0.5% skim milk, and 0.25 mg/ml bovine sperm DNA). A probe is prepared by digesting the plasmid used for the transformation with EcoRI and HindIII in the same manner as described above, performing ethanol precipitation, washing with 70% ethanol, and drying, and dissolving the digested product in redistilled water (5 µl). An obtained preparation is added with a dye for electrophoresis (1 µl) to perform fractionation by means of 0.8% agarose gel electrophoresis (GTG agarose gel produced by FMC Seachem, TBE buffer) so that a DNA fragment containing the pyruvate kinase antisense DNA is recovered from the agarose gel. An aliquot of the DNA fragment (25 ng) is prepared by using [$\alpha$-$^{32}$P]dCTP and Multiprime Labeling Kit produced by Amersham. The thermally denatured probe is mixed with a hybridization solution (0.1 g dextran sulfate/ml prehybridization solution). The hybridization solution is scattered and spread on the cut membrane from which removed prehybridization solution, followed by being left to stand at 42° C. overnight. Shaking is performed at room temperature for 15 minutes in 2×SSC solution (100 ml) containing 0.1% SDS, and this operation is repeated twice. Further, washing is performed for 15 minutes in the same manner as described above in 1×SSC solution (100 ml) containing 0.1% SDS, and this operation is repeated twice. Specific binding formed by the probe is detected by autoradiography. Expression of the pyruvate kinase antisense DNA in a seed is inspected by extracting total RNA of the seed in accordance with an ordinary method, for example, in accordance with a method described in "Molecular Cloning", and performing Northern analysis by using the introduced antisense portion as a probe. Further, the degree of expression of the pyruvate kinase antisense DNA can be judged by measuring the enzyme activity of pyruvate kinase.

In the present invention, not only the activity of pyruvate kinase is lowered as described above, but also the activity of phosphoenolpyruvate carboxylase can be simultaneously lowered. Thus the storage lipid content in seed of the plant can be further increased. The activity of phosphoenolpyruvate carboxylase can be also lowered in the same manner as described above for the case of pyruvate kinase in accordance with a method for introducing, into the objective plant, the DNA sequence coding for phosphoenolpyruvate carboxylase or a part thereof in a form to suppress transcription and/or translation of the phosphoenolpyruvate carboxylase gene.

Those known as the DNA sequence coding for phosphoenolpyruvate carboxylase include genes of tobacco (*Plant*

Mol. Biol., 17, 535–539, 1991), sorghum (Gene, 99, 87–94, 1991), ice plant (Nuc. Acids Res., 17, 6743–6741, 1989), corn (Plant Mol. Biol., 12, 579–589, 1989), and Escherichia coli (Plant Mol. Biol., 21, 487–502, 1993). It is also possible to use those isolated from mRNA of a plant body in accordance with the PCR by using primers prepared on the basis of the foregoing known gene sequences in the same manner as the case of pyruvate kinase described above. The DNA sequence coding for phosphoenolpyruvate carboxylase or the part thereof can be introduced into the plant in accordance with a method similar to those used for pyruvate kinase described above, i.e., the antisense method, the co-suppression method, the ribozyme method, and the gene targeting method.

The DNA sequence coding for pyruvate kinase and the DNA sequence coding for phosphoenolpyruvate carboxylase may be introduced into cell by using an identical vector or by using different vectors.

The plant has been transformed by using the vector having the seed-specific expression promoter introduced with the pyruvate kinase antisense DNA or simultaneously introduced with the pyruvate kinase antisense DNA and the phosphoenolpyruvate carboxylase antisense DNA. Thus the lipid content in seed can be increased more conveniently and reliably than those obtained by the conventional method.

DETAILED DESCRIPTION OF THE PREFERRED EMBODIMENT(S)

Figure 1:
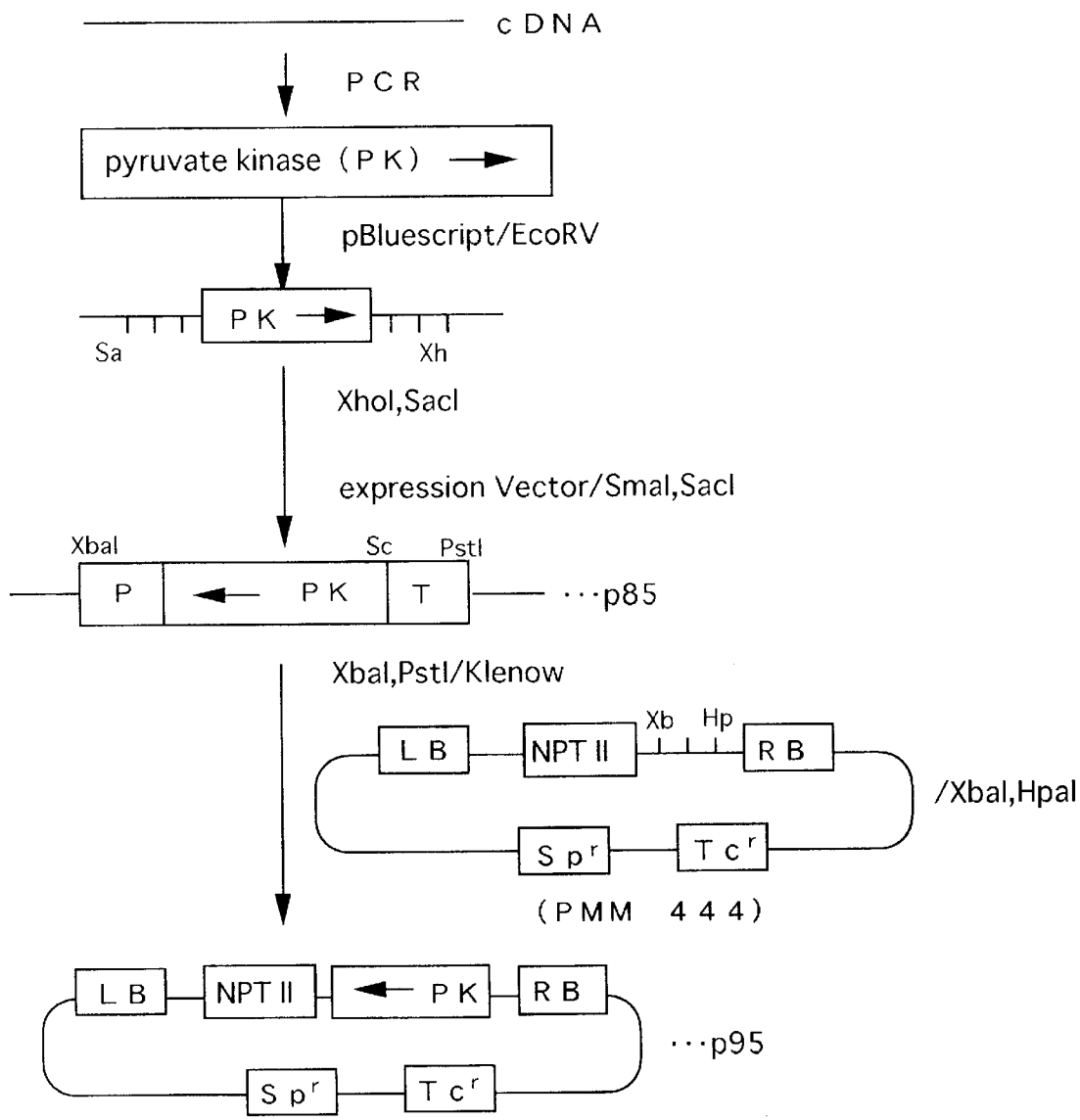
FIG. 1 shows construction of vectors according to the present invention.

The present invention will be explained below with reference to Examples. However, the present invention is not limited to the following Examples provided that the gist the present invention is not exceeded.
(1) Construction of vectors At first, mRNA was extracted from seeds of B. napus cv. Westar in accordance with a method described in "Molecular Cloning". Namely, an appropriate amount of liquid nitrogen was added to about 750 mg of the immature seeds placed in a mortar, and the seeds were well ground by using a pestle. A mRNA-extracting solution (3 ml, Tris-HCl buffer containing 1% (w/v) SDS) and an equal amount of phenol were added thereto, followed by further grinding. Extracted matters were transferred to a tube to perform centrifugation at 4,000 rpm for 10 minutes. An aqueous layer was recovered, to which phenol and chloroform in a half amount of the aqueous layer respectively were added to perform agitation, followed by centrifugation again. An aqueous layer was obtained, to which an equal amount of chloroform was added, followed by agitation and centrifugation. An aqueous layer was recovered, to which a 1/100 amount of 10 M lithium chloride aqueous solution and 2-fold amount of ethanol were added, followed by being left to stand at −20° C. for not less than 1 hour. Centrifugation was performed at 10,000×g for 5 minutes to obtain a precipitate which was washed with 70% ethanol and then dried to be dissolved in 1 ml of sterilized water. A 1/5 amount of 10 M lithium chloride aqueous solution was added to the obtained solution, which was left to stand in ice overnight, followed by centrifugation at 10,000×g for 10 minutes to recover a precipitate. The precipitate was dissolved in sterilized water again to be used as total RNA. The total RNA was applied to an oligo dT cellulose column to purify mRNA.

Next, cDNA was synthesized from the obtained mRNA. Namely, respective cDNA's were synthesized in accordance with a protocol for cDNA Synthesis Kit (produced by Takara Shuzo) by using 1 to 2 μg of mRNA, 1 μg of oligo (dT) primer, and a sequence of a complementary strand of 5'-CATTGATTCAAGCATCTGAGTNGC-3' (SEQ ID NO: 3) for cytosolic pyruvate kinase or a sequence of a complementary strand of 5'-AAGCACTACATAGAATTTTGGA-3' (SEQ ID NO: 7) for phosphoenolpyruvate carboxylase.

A half amount of obtained cDNA was subjected to the PCR. Sequences of portions having high homology selected from sequences of cytosolic pyruvate kinase and phosphoenolpyruvate carboxylase having been published for other plants were used for primers. Namely, 5'-CTTGACACCAAGGGGCCTGAA(G)AT-3' (SEQ ID NO: 2) and a sequence of a complementary strand for the sequence described in SEQ ID NO: 3 were used for pyruvate kinase, and 5'-TTTCATGAAACTATTTGGAAGGG-3' (SEQ ID NO: 6) and a sequence of a complementary strand for the sequence described in SEQ ID NO: 7 were used for phosphoenolpyruvate carboxylase. The PCR was carried out by using DNA Thermal Cycler produced by Perkin Elmer Ceuts and using a reaction solution (100 μl) prepared by mixing reagents in accordance with a protocol for Gene-Amp Kit produced by Perkin Elmer Ceuts. The reaction was performed for pyruvate kinase by repeating a cycle 25 to 30 times, each cycle comprising thermal denaturation at 94° C. for 20 seconds, annealing at 42° C. for 30 seconds, and elongation reaction with heat-resistant polymerase at 72° C. for 1 minute. The reaction was performed for phosphoenolpyruvate carboxylase by repeating a cycle 35 times, each cycle comprising annealing at 46° C. for 15 seconds and elongation reaction at 72° C. for 30 seconds without thermal denaturation.

In order to ensure that the DNA fragments obtained as described above were those concerning pyruvate kinase and phosphoenolpyruvate carboxylase, the second PCR was performed. In this procedure, thermal denaturation was not performed for pyruvate kinase, and a cycle was repeated 25 to 30 times, each cycle comprising annealing at 44° C. for 15 seconds and elongation reaction with heat-resistant polymerase at 72° C. for 1 minute. Primers used were sequences of complementary strands of 5'-CTTGACACCAAGGGGCCTG-3' (SEQ ID NO: 4) and 5'-GAGATCACCTCGAGCAACCAT-3' (SEQ ID NO: 4). In order to increase reliability, this procedure was designed such that amplification was performed by using the primer used for the 3'-side (SEQ ID NO: 5) which was a different primer sequence corresponding to a portion located inside as compared with the primer (SEQ ID NO: 3) used for the first PCR. The same primer as that used for the first PCR was used for phosphoenolpyruvate carboxylase, and a cycle was performed 35 times, each cycle comprising annealing at 50° C. for 5 seconds and elongation reaction at 72° C. for 30 seconds without thermal denaturation. In this case, the reaction was designed so that reliability is increased by raising the annealing temperature.

A 1/20 amount of the final PCR reaction solution was separated by means of agarose gel electrophoresis to detect amplified bands. The antisense DNA of pyruvate kinase corresponded to a band of 555 bp, and the antisense DNA of phosphoenolpyruvate carboxylase corresponded to a band of 343 bp. These DNA fragments were separated by using 1% GTG agarose gel produced by FMC Seachem. Band portions of the objective sizes were excised respectively, followed by melting by means of a treatment at 55° C. for 15 seconds. After that, the DNA fragments were purified with phenol and a mixed solution of phenol and chloroform (1:1), and then recovered by means of ethanol precipitation. The obtained two DNA fragments were subjected to a Klenow treatment respectively to convert them into blunt-ended DNA fragments, followed by a treatment with T4 polynucleotide kinase. The DNA fragments were purified again with a mixed solution of phenol and chloroform (1:1), and they were inserted into an EcoRV site of pBluescript plasmid (produced by STRATAGENE) respectively.

The sequence (SEQ ID NO: 1) obtained by sequencing the cDNA insert fragment of cytosolic pyruvate kinase was compared for homology with sequences of cytosolic pyruvate kinases reported for other plants. Thus the obtained sequence was confirmed to be cDNA coding for the cytosolic pyruvate kinase expressing in rapeseed. This plasmid was digested at an XhoI site, followed by a Klenow treatment to convert it to have blunt ends. After that, the plasmid was digested at a SacI site. The DNA fragment containing the amplified DNA fragment was inserted into SmaI, SacI sites of an expression vector (pNap, Japanese Patent No. 5–073806) for seed-specifically expressing the DNA fragment. In this procedure, a plasmid was selected, in which the amplified cDNA fragment of pyruvate kinase was inserted in a direction opposite to that of the original sequence of the enzyme. This plasmid is hereinafter referred to as p85.

Sequences of complementary strands, i.e., 5'-GTGTTCCTTACAACGCTCCTCTC-3' (SEQ ID NO: 8) for a 5'-side primer and 5'-CAGAAGCTCAAAGG TGTGCCAAA-3' (SEQ ID NO: 9) for a 3'-side primer were selected from a sequence obtained by sequencing the cDNA insert fragment of phosphoenolpyruvate carboxylase. The sequences were used as primers, and genome DNA of rapeseed (10 ng) was used as a temperate so that a cycle was repeated 35 times, each cycle comprising annealing at 52° C. for 10 seconds and elongation reaction at 72° C. for 1 minute without thermal denaturation. An amplified fragment of about 340 bp thus obtained was separated by using 1% GTG agarose gel produced by FMC Seachem. A band portion of the objective size was excised, followed by melting by means of a treatment at 55° C. for 15 seconds. After that, the DNA fragment was purified with phenol and a mixed solution of phenol and chloroform (1:1), and the DNA fragment was recovered by means of ethanol precipitation. The obtained DNA fragment was subjected to a Klenow treatment to convert it into a blunt-ended DNA fragment, followed by a treatment with T4 polynucleotide kinase. The DNA fragment was purified again with a mixed solution of phenol and chloroform (1:1), and it was inserted into an EcoRV site of pBluescript plasmid.

The sequence (SEQ ID NO: 10) obtained by sequencing the DNA insert fragment of phosphoenolpyruvate carboxylase was compared for homology with sequences of phosphoenolpyruvate carboxylase reported for other plants. Thus the obtained sequence was confirmed to be DNA fragment coding for phosphoenolpyruvate carboxylase of rapeseed containing two introns. This plasmid was digested at a HindIII site, followed by a Klenow treatment to convert it to have blunt ends. After that, the plasmid was digested at a SacI site. The DNA fragment containing the amplified DNA fragment was inserted into SmaI, SacI sites of an expression vector for seed-specifically expressing the DNA fragment. In this procedure, a plasmid was selected, in which the amplified DNA fragment of phosphoenolpyruvate carboxylase was inserted in a direction opposite to that of the original sequence of the enzyme. This plasmid is hereinafter referred to as p84.

Next, DNA fragment of phosphoenolpyruvat carboxylase and cDNA of pyruvate kinase were ligated as follows. p84 was treated with XbaI and SpeI to recover a DNA fragment containing the phosphoenolpyruvate carboxylase gene which was ligated with a plasmid obtained by treating p85 with XbaI and BAP. This plasmid is hereinafter referred to as p845. These plasmids (p85, p845) were used when transformation was performed in accordance with the electroporation method.

Next, plasmids to be used for the Agrobacterium method were constructed as follows. A plasmid (pMM444) having a tetracycline resistance gene and a spectinomycin resistance gene as selection markers for *Escherichia coli*, and a kanamycin resistance gene as a selection marker for the plant was digested with XbaI and HpaI, and the vector DNA was purified by means of phenol treatment and ethanol precipitation. p85 and p845 were treated with PstI, and then blunt-ended by means of a Klenow treatment. Then the fragments were further digested with XbaI and purified in the same manner as the vector DNA fragment. A DNA fragment containing cDNA of pyruvate kinase, or a DNA fragment containing DNA coding for phosphoenolpyruvate carboxylase and cDNA of pyruvate kinase was recovered and ligated with the foregoing pMM444. These plasmids are hereinafter referred to as p95, p945.

These plasmids (p95, p945) were used to transform Agrobacterium EHA101 strain in accordance with a method described in "DNA Cloning".

A single colony of EHA101 was cultivated overnight in YEB medium (0.1% Yeast extract, 0.5% Beef extract, 0.5% peptone, and 0.5% sucrose, pH 7.0). An aliquot (1 ml) of an obtained culture was added to YEB medium containing 25 μg/ml of kanamycin, 12.5 μg/ml of chloramphenicol, 25 μg/ml of spectinomycin, and 1 μg/ml of tetracycline, followed by cultivation at 30° C. for 5 to 6 hours. An obtained culture liquid was centrifuged at 4,000 rpm for 5 minutes to obtain a precipitate to which 20 ml of 10 mM Tris-HCl buffer (pH 8) was added to perform washing. The recovered precipitate was suspended in 400 μl of YEB medium. An aliquot (90 μl) of the suspension was combined with the foregoing p95 of p945 plasmid (10 ng/10 μl), followed by treatments at −110° C. for 5 minutes and subsequently at 37° C. for 25 minutes. The treated suspension was added with 400 μl of YEB medium to perform cultivation with shaking at 30° C. overnight. An aliquot (50 μl) of an obtained culture liquid was spread over YEB agar medium containing 50 μg/ml of kanamycin, 25 μg/ml of chloramphenicol, 50 μg/ml of spectinomycin, and 2 μg/ml of tetracycline, followed by cultivation at 30° C. for 2 days to select colonies containing the plasmid. Culture liquids (each 1 ml) originating from these colonies were prepared, from which DNA's were prepared by means of the alkali SDS method in accordance with a method described in "Molecular Cloning". Total amounts of DNA's were digested with a restriction enzyme EcoRI (for p95) or BqlII (for p945) respectively by using 10 μl of a reaction system containing 0.5 μg/ml of RNase at 37° C. for 30 minutes. Thus a clone harboring the plasmid was selected.

(2) Transformation (a) Agrobacterium-mediated transformation

Seeds of *B. napus* cv. *Westar* were treated with 10% aqueous hydrogen peroxide solution for 25 minutes washed with sterilized distilled water in several times, and dried. The seeds were cultivated on MS agar medium under illumination (1,000 to 4,000 luxes) for 2 to 3 weeks. An obtained aseptic hypocotyl was cut into pieces having lengths of 2 to 5 mm which were placed on a pre-cultivation medium (medium obtained by spreading an appropriate amount of cultured tobacco cells BY-2 all over MS agar medium containing B-5 vitamin, 1 mg/l 2,4-dichlorophenoxyacetic acid, 3% sucrose, and 0.7 agarose, covered with sterilized filter paper) to perform pre-cultivation overnight at a light place. A colony of Agrobacterium having the p95 of p945 plasmid was cultivated in 5 ml of YEB liquid med ium at 30° C. overnight. An obtained culture medium was centrifuged a t 3,000 rpm for 10 minutes. Bacterial cells were washed with MS liquid medium containing 3% sucrose, and then suspended in the same MS medium. This suspension of Agrobacterium w as added with the pre-cultivated hypocotyl, followed by cultivation with shaking at 25° C. for 5 to 20 minutes. This solution was filtrated to take out only the hypocotyl. Excessive Agrobacterium was removed on a sterilized paper towel, followed by simultaneous cultivation on the original pre-cultivation medium for 2 days so that the hypocotyl was infected with Agrobacterium.

After that, the pieces of hypocotyl were transferred to a medium for removing the bacterium (MS agar medium containing B-5vitamin, 1 mg/l 2,4-dichlorophenoxyacetic acid, 3% sucrose, 0.7% agarose, and 500 mg/l carbenicillin), followed by cultivation for 3 days to suppress proliferation of Agrobacterium. Next, the pieces of hypocotyl were transferred onto a primary selection medium (MS agar medium containing B-5 vitamin, 3 mg/l benzylaminopurine, 1 mg/ml zeatin, 2% sucrose, 0.7% agarose, 30 mg/ml kanamycin, and 500 mg/l carbenicillin), followed by cultivation for 2 weeks. Thus only transformed plant cells having the p95, p945 plasmids brought about by the infection with Agrobacterium were allowed to divide and proliferate, making it possible to form green calluses. Further, the pieces of hypocotyl were transferred onto a secondary selection medium (the same medium as the primary selection medium except that the sucrose content was decreased from 2% to 1%), followed by cultivation for 3 weeks. At this stage, the transformed calluses further grew. Accordingly, only the callus portions were then transferred onto a germination medium (the same medium as the secondary selection medium except that kanamycin was removed, and carbenicillin was decreased from 500 mg/l to 250 mg/l). The reproduced buds were allowed to grow on a growth medium (B5 agar medium containing 0.1 mg/l benzylaminopurine, 250 mg/l carbenicillin, and 0.7% agarose), followed by transfer onto a rooting medium (MS agar medium containing 0.1 mg/l 1-naphthalene acetic acid, 0.01 mg/l benzylaminopurine, 3% sucrose, and 0.8% agarose), and then they were acclimatized and conditioned.

(b) Transformation by electroporation

Aseptically germinated hypocotyl was cut into pieces of about 1 mm in an enzyme solution (MS medium-inorganic salt solution containing 2% cellulase RS, 0.01% pectolyase Y-23, 0.5 M sucrose, and 0.01% MES, pH 5.7), followed by gentle shaking at 25° C. for 6 hours. After completion of the enzyme treatment, undigested matters were removed by filtration to obtain a filtrate which was transferred to a centrifugation tube. A ½₀ amount of washing solution (125 mM calcium chloride, 156 mM sodium chloride, 5 mM potassium chloride, and 5 mM glucose, pH 5.8) was layered thereon, followed by centrifugation at 300 rpm for 5 minutes. An obtained protoplast fraction was transferred to a new centrifugation tube, to which an appropriate amount of the washing solution was added, followed by centrifugation at 300 rpm for 5 minutes again to obtain protoplasts.

Next, the obtained protoplasts were suspended at a concentration of 6×105 individuals/ml in an electroporation suspension solution (0.4 M mannitol, 5 mM magnesium chloride, 70 mM potassium chloride, 0.1% MES, pH 5.5). This suspension (0.5 ml) was added with the plasmid (p85 or p845) containing the antisense DNA of pyruvate kinase, and bovine sperm gene, so that the former had a concentration of 40 µg/ml and the latter had a concentration of 40 µg/ml. After that, electric pulse was applied (electric capacitance: 400 µF, voltage: 600 V/cm, time: 7.5 milliseconds) by using X-Cell 450 (produced by Promega) to perform transformation.

The protoplasts subjected to the electroporation treatment were cultivated for 1 week in KM8p medium containing 0.4 M glucose, 1 mg/l 2,4-dichlorophenoxyacetic acid, 0.1 mg/l naphthalene acetic acid, and 0.4 mg/l benzylaminopurine. After that, transformed cells were selected by adding 10 mg/l kanamycin. Transformed calluses obtained after 3 weeks were transferred to CN medium, DN medium, K3 medium, B5 medium, and MS medium each containing 10 mg/l kanamycin at every 3 weeks to obtain reproduced individuals.

(3) Selection and regeneration of calluses introduced with antisense DNA of pyruvate kinase or antisense DNA's of both pyruvate kinase and phosphoenolpyruvate carboxylase Genome DNA's were prepared from the regenerated plant obtained by the foregoing both transformation methods. PCR was performed by using parts of the introduced plasmids as primers. Thus the plant was further selected, in which the antisense DNA of pyruvate kinase or the antisense DNA's of both pyruvate kinase and phosphoenolpyruvate carboxylase were introduced. Genome DNA was prepared as follows in accordance with a method described in *Mol. Gen. Genet.*, 211, pp. 27–34, 1988. The kanamycin-resistant plant (50 to 100 mg) was ground in buffer (15% sucrose, 50 mM Tris-HCl (pH 8), 50 mM NaEDTA, 500 mM sodium chloride), and a nucleus fraction was separated by centrifugation. The obtained fraction was treated with a detergent solution (1.5% sodium dodecyl sulfate, 20 mM Tris-HCl (pH 8), 10 mM EDTA). Extracts of nucleus fraction were precipitated with a 0.6 volume of isopropanol to obtain nucleic acid which was washed with 70% ethanol, followed by drying to prepare a genome fraction. This fraction (300 ng) was subjected to the PCR. In this procedure, the following primers were used to perform amplification. Namely, a part of the sequence of the seed-specific expression promoter portion was used for the 5'-side, and a part of the antisense DNA sequence of pyruvate kinase (SEQ ID NO: 3) or a part of the antisense DNA sequence of phosphoenolpyruvate carboxylase (SEQ ID NO: 9) was used for the 3'-side. PCR was performed by repeating a cycle 30 times, each cycle comprising thermal denaturation at 94° C. for 15 seconds, annealing at 42° C. for 30 seconds, and elongation reaction at 72° C for 1 minute. After the reaction, the reaction solution (10 µl) was analyzed by means of agarose gel electrophoresis to detect amplified bands. The plants were allowed to undergo potting respectively in order that plant for which the introduced gene was confirmed by the PCR were used as transformants, and plant for which no introduced gene was confirmed were used as controls. Thus self-propagation seeds were obtained after 3 to 6 months.

(4) Confirmation of expression of antisense DNA of pyruvate kinase or antisense DNAs of pyruvate kinase and phosphoenolpyruvate carboxylase in transgenic seeds (a) Measurement of pyruvate kinase activity Pyruvate kinase was extracted and measured for its activity as follows in accordance with a method established for castor bean (*Plant Physiol.*, 86, 1064–1069, 1988).

Immature seeds of non-transformed *B. napus* cv. *Westar* were used as a control. Ten individuals of the transgenic immature seeds with the increased lipid content and ten individuals of the control immature seeds were used, to which 0.5 ml of an enzyme extraction solution (100 mM sodium phosphate buffer containing 0.5 M sucrose, 0.5 mM EDTA, 0.5 mM dithioerythritol, 1 mM manganese chloride, and 1 mM PMSF, pH 7.5) was added respectively, followed by grinding. Each of obtained samples was centrifuged at 3,000 rpm for 5 minutes. An obtained supernatant was further centrifuged at 14,000 rpm for 10 minutes, and its supernatant was heat-treated at 60° C. for 4 minutes to prepare a crude enzyme solution of the cytosolic pyruvate kinase.

The protein content was measured by using 1 µl of the crude enzyme solution in accordance with a method described for Bio Rad Protein Assay Kit (produced by Bio Rad). The pyruvate kinase activity was measured as follows. Namely, the crude enzyme solution was added so that an amount of 50 pg of protein was contained in 1 ml of an enzyme reaction solution (0.5 M Hepes-water-sodium hydroxide buffer containing 10 mM magnesium chloride, 50 mM potassium chloride, 0.2 mg/ml bovine serum albumin, 2 mM dithioerythritol, 2 U lactate dehydrogenase, 0.15 mM NADH, 2 mM ADP, and 2 mM phosphoenolpyruvic acid, pH 6.9). Thus the change in absorbance at 340 nm was measured for 30 seconds. Measurement was performed in the same manner as described above except that the same amount of the enzyme solution was added to an enzyme reaction solution not containing 2 mM ADP to obtain a background value for each crude enzyme solution. The obtained value was subtracted from a value obtained by measurement with the foregoing reaction solution containing ADP to determine a true pyruvate kinase activity. The activity was represented such that 1 Unit corresponded to consumption of 1 µmol of NADH per 1 mg of protein and 1 minute of reaction time. Results are shown in Table 1. According to the results, it was confirmed that the activity of the cytosolic pyruvate kinase was decreased by introducing the antisense gene of the cytosolic pyruvate kinase.

TABLE 1

| Measured plant individual | Cytosolic pyruvate kinase activity | |
|---|---|---|
| | 24 days after fertilization | 28 day after fertilization |
| control | 1.94 | 1.26 |
| p95-introduced individual | 0.92 | 0.64 |

(b) Measurement of lipid content

Reproduced individual having no introduced gene and mature seed of non-transformed *B. napus* cv. *Westar* were used as controls. The obtained transformant and the controls (each about 2 g) were heated at 100° C. for 2 hours to remove water content. After that, the samples were disrupted by using a mill or the like, followed by division into approximately equal amounts to measure their weights. Each of a half amount of the disrupted matter was used to extract crude lipid with a solvent of diethyl ether by using Soxhlet extractor. The extracted crude lipid was dried, and its mass was measured. The lipid content was determined in % by weight. The measurement was performed twice for one individual. An obtained average value was regarded as a lipid content of the individual. Results are shown in Table 2. According to the results, it was confirmed that the lipid content was increased by introducing the antisense DNA of pyruvate kinase or the antisense DNA's of both pyruvate kinase and phosphoenolpyruvate carboxylase.

TABLE 2

| Measured plant | Total lipid content (%) |
|---|---|
| control | 36.1 ± 3.5 |
| p95-introduced plant #1 | 42.0 |
| p95-introduced plant #2 | 41.9 |
| p95-introduced plant #3 | 39.6 |
| p945-introduced plant #1 | 46.6 |
| p945-introduced plant #1 | 44.8 |

(5) Heredity, to progenies, of increase in storage lipid content in seed, antisense DNA of pyruvate kinase, or antisense DNAs of both pyruvate kinase and phosphoenolpyruvate carboxylase Self-propagation seeds were obtained from transformant with p95 and with p-945 in which the lipid content was increased at the regenerants. The self-propagated seeds were germinated to obtain individuals (progenies) with their leaves from which genome DNAs were prepared to confirm heredity, to progenies, of the antisense DNA of pyruvate kinase or the antisense DNAs of both pyruvate kinase and phosphoenolpyruvate carboxylase by means of PCR. Further, the lipid content was measured for self-propagated seeds born by the progeny plant in the same manner as described in the item (4). Results are shown in Table 3. According to the results, it was confirmed that the lipid content was increased in the progenies having the antisense gene of pyruvate kinase or the antisense genes of both pyruvate kinase and phosphoenolpyruvate carboxylase.

TABLE 3

| Measured plant individual | Total lipid content (%) |
|---|---|
| progeny with no gene | 36.1 ± 3.5 |
| p95-harboring selfed progeny plant #1 | 44.3 |
| p-945-harboring selfed progeny plant #2 | 47.0 |

What is claimed is:

1. A method for increasing a storage lipid content in a seed of a plant, comprising the step of:
   introducing into the plant a DNA having a sequence coding for pyruvate kinase or a part thereof, wherein by an antisense method or a co-suppression method, expression of cytosolic pyruvate kinase in cells of the seed is suppressed, thereby substantially lowering an activity of cytosolic pyruvate kinase in the seed of the plant as compared with an endogenous activity of cytosolic pyruvate kinase in the seed of the plant, to thereby increase the storage lipid content of the seed.

2. The method according to claim 1, wherein the plant is a plant which accumulates storage protein and storage lipid in its embryo.

3. The method according to claim 1, wherein the plant is an oilseed plant.

4. The method according to claim 1, wherein the plant is rapeseed, soybean, sunflower, or sesame.

5. The method according to claim 4, wherein the plant is rapeseed.

6. The method according to claim 1, further comprising the step of substantially lowering an activity of phosphoenolpyruvate carboxylase as compared with an endogenous activity of phosphoenolpyruvate carboxylase in the seed of the plant.

7. A transformed plant obtained by the method as defined in claim 6, which provides an increased storage lipid content in its seed.

8. A seed of a transformed plant obtained by the method as defined in claim 6, which provides an increased storage lipid content in the seed.

9. A transformed plant obtained by the method as defined in claim 1, which provides an increased storage lipid content in its seed.

10. A seed of a transformed plant obtained by the method as defined in claim 1, which provides an increased storage lipid content in the seed.

11. The method according to claim 1, wherein the DNA having a sequence coding for pyruvate kinase is a cytosolic pyruvate kinase gene of rapeseed, castor bean, potato, soybean or rice, or an endogenous pyruvate kinase gene in the plant, or a part thereof.

12. The method according to claim 11, wherein the DNA having a sequence coding for pyruvate kinase is selected from the group consisting of:
   (a) a DNA having the sequence defined in any one of SEQ ID NOS: 1, 11, 12, 13, 14 or 15, or a part thereof; and
   (b) a DNA hybridizable under physiological conditions with the DNA having the sequence as defined in (a), or an RNA having a sequence homologous thereto, or a part thereof.

13. The method according to claim 1, wherein the DNA sequence coding for pyruvate kinase or the part thereof is introduced into the plant by an antisense method in such a manner as to suppress expression of cytosolic pyruvate kinase in cells of the seed.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 498 base pairs (B) TYPE: nucleic acid
        (C) STRANDEDNESS: double
        (D) TOPOLOGY: linear (ii) MOLECULE TYPE: cDNA to mRNA (iv) ANTI-SENSE: NO (vi) ORIGINAL SOURCE:
        (A) ORGANISM: B. napus cv. Westar (xi) SEQUENCE DESCRIPTION: SEQ ID NO: 1:

```
CGTACTGGTT TCTTGAAAGA TGGGAACCCT ATACGACTCA AGGAAGGTCC GGAGATCACT      60

ATCACCACTG ACTATGAAAC TTTAGGAGAT GAGACGACGA TCTCCATGAG CTATAAGAAG     120

CTTCCCTTAG ATGTGAAGCC CGGAAACACC ATTCTCTGTG CAGATGGAAG CATAAGTCTA     180

GCTGTCTTAT CATGTGATCC AGAGTCTGAA ACTGTTAGGT GCAGGTGCGA AAACACGGCG     240

ATGCTTGGCG AGAGAAAGAA CGTGAATCTC CCCGGTGTCG TTGTTGATCT CCCCACTCTG     300

ACAGACAAGG ATATTGAAGA TATTATGGGT TGGGGTGTTC CTAACAGCAT CGATATGATT     360

GCGCTTTCTT TTGTCCGTAA AGGCTCAGAT CTTGTTAATG TCAGGAGGGT TCTTGGTTCT     420

CATGCTAAAA GCATAATGCT GATGTCAAAG GTTGAGAACC AGGAGGGAGT TGTTAACTTT     480

GATGAGATAC TGCGCGAA                                                   498
```

(2) INFORMATION FOR SEQ ID NO: 2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Synthetic DNA"

(xi) SEQUENCE DESCRIPTION: SEQ ID NO: 2:

```
CTTGACACCA AGGGGCCTGA RAT                                              23
```

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Synthetic DNA"

(xi) SEQUENCE DESCRIPTION: SEQ ID NO: 3:

```
CATTGATTCA AGCATCTGAG TNGC                                             24
```

(2) INFORMATION FOR SEQ ID NO: 4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Synthetic DNA"

(xi) SEQUENCE DESCRIPTION: SEQ ID NO: 4:

```
CTTGACACCA AGGGGCCTG                                                   19
```

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 5:

```
GAGATCACCT CGAGCAACCA T                                              21
```

(2) INFORMATION FOR SEQ ID NO: 6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 6:

```
TTTCATGAAA CTATTTGGAA GGG                                            23
```

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 7:

```
AAGCACTACA TAGAATTTTG GA                                             22
```

(2) INFORMATION FOR SEQ ID NO: 8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 8:

```
GTGTTCCTTA CAACGCTCCT CTC                                            23
```

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 9:

```
CAGAAGCTCA AAGGTGTGCC AAA                                            23
```

5,914,449

21                                                                      22
-continued (2) INFORMATION FOR SEQ ID NO: 10:

(i) SEQUENCE CHARACTERISTICS:
       (A) LENGTH: 373 base pairs
       (B) TYPE: nucleic acid
       (C) STRANDEDNESS: double
       (D) TOPOLOGY: linear (ii) MOLECULE TYPE: DNA (genomic)

(iv) ANTI-SENSE: NO (vi) ORIGINAL SOURCE:
        (A) ORGANISM: B. napus cv. Westar (xi) SEQUENCE DESCRIPTION: SEQ ID NO: 10:

```
GTGTTCCTTA CAACGCTCCT CTCATTCAGT TCTCTTCCTG GATGGGTGGA GACCGTGATG      60

GTACCCTACA CTCTTATTAT TACTTCTGTA TCCTCTTGAA AACATGATTT TAACTATCAA     120

ACATGTCTTA ATCCAGGAAA CCCTCGAGTC ACTCCTGAAG TTACAAGAGA TGTATGCTTA     180

CTAGCAAGAA TGATGGCTGC TAATCTCTAC TTCTCCCAGA TTGAAGAACT TATGTTCGAA     240

GTGAAGAAAC GTTTTAACTC ATCACAGCTT CCTTAGTTTC TTTGGTAGTT AANGTTAGGT     300

TTATTGGCAG ATGTCCATGT GGCGTTGCAA TGAGGAACTT CGTGTTCGAG CAGAAGCTCA     360

AAGGTGTGCC AAA                                                        373
```

(2) INFORMATION FOR SEQ ID NO: 11:

(i) SEQUENCE CHARACTERISTICS:
       (A) LENGTH: 2006 base pairs
       (B) TYPE: nucleic acid
       (C) STRANDEDNESS: double
       (D) TOPOLOGY: linear (ii) MOLECULE TYPE: cDNA to mRNA (iv) ANTI-SENSE: NO (vi) ORIGINAL SOURCE:
        (A) ORGANISM: potato (Solanum tuberisum)

(ix) FEATURE:
        (A) NAME/KEY: CDS
        (B) LOCATION: 99..1628

(xi) SEQUENCE DESCRIPTION: SEQ ID NO: 11:

```
CCTGGCAAAA GCACAAGAAA CAAACAGTAG CACTAAAATC TTGAAGGGGT GGTTTAGCTT      60

GATCTGTAGC TTTTGTTAGT GACTGATAAA TAGAAGAAAT GGCCAACATA GACATAGCTG     120

GAATCATGAA GGATCTCCCA AATGATGGCC GTATTCCAAA GACCAAGATT GTTTGCACGT     180

TAGGGCCATC TTCTAGAACA GTGCCAATGC TGGAGAAGCT TCTCCGTGCT GGCATGAACG     240

TTGCCAGGTT TAACTTTTCT CATGGGACCC ATGAGTACCA TCAGGAGACA TTGGACAATC     300

TTAAGATTGC TATGCAGAAT ACTCAGATCC TGTGTGCTGT CATGCTTGAC ACCAAGGGGC     360

CTGAGATTCG TACTGGTTTC TTAACAGATG GAAAACCGAT TCAGCTTAAG GAAGGTCAAG     420

AAATCACTGT ATCCACAGAC TATACCATAA AGGAAATGA AGAAATGATC TCAATGAGCT     480

ATAAGAAGTT GGTAATGGAC TTGAAGCCCG GCAATACCAT TTTGTGTGCA GATGGTACCA     540

TAACCCTTAC TGTTTTGTCA TGTGATCCAC CGTCTGGAAC GGTGAGATGT CGCTGCGAGA     600

ATACTGCCAC CTTAGGAGAG AGGAAGAATG TAAACCTTCC AGGTGTGGTT GTGGACCTTC     660

CAACACTTAC AGAAGAGGAT AAAGAAGATA TACTAGAGTG GGGTGTTCCT AACAACATTG     720

ATATGATAGC GCTTTCGTTT GTGCGTAAGG GTTCAGATCT TGTCAATGTT CGCAAGGTTC     780

TTGGTCCACA TGCCAAGCGC ATTCAACTAA TGTCAAAGGT TGAAAACCAA GAAGGGGTAA     840
```

```
TCAACTTTGA TGAAATCCTT CGTGAGACAG ATTCTTTTAT GGTTGCTCGA GGTGATCTCG      900

GAATGGAAAT TCCAGTTGAG AAGATTTTCT TGGCTCAGAA AATGATGATA TACAAGTGTA      960

ATCTTGCTGG CAAAGCTGTG GTAACTGCCA CTCAGATGCT TGAATCAATG ATCAAGTCTC     1020

CAGCACCCAC CCGTGCTGAG GCTACTGATG TGGCTAATGC TGTCTTGGAT GGCACTGATT     1080

GTGTTATGTT AAGTGGGGAG AGTGCAGCTG GTGCTTATCC TGAGCTGGCA GTAAAAATCA     1140

TGTCACGAAT CTGCATTGAG GCAGAGTCTT CACTTGACAA CGAGGCTATC TTCAAGGAAA     1200

TGATCAGGTG TACCCCACTG CCAATGAGCC CATTGGAGAG TCTTGCATCA TCAGCTGTCC     1260

GTACGGCTAA CAAAGCTAGA GCAAAACTCA TTGTTGTCCT GACACGTGGC GGGAGTACAG     1320

CAAAGCTGGT TGCCAAGTAT AGGCCTGCAG TTCCTATTCT GTCAGTAGTC GTGCCTGTTT     1380

TGACCACAGA CTCTTTCGAT TGGTCCATCA GCGACGAGAC CCCAGCTAGA CACAGTTTGG     1440

TATATAGGGG CTTGATTCCA CTTCTTGGTG AAGGTTCTGC AAAGGCCACT GATTCTGAAT     1500

CAACTGAGGT AATCCTTGAA GCGGCCCTGA AGTCTGCCGT AACGAGAGGG CTATGCAAAC     1560

CTGGTGATGC TGTCGTGGCA CTTCATCGTA TTGGTTCTGC ATCCGTTATC AAGATTTGCG     1620

TCGTGAAGTA ATCGTCGTGT CACATAACAT ACAAATCTTG AACTCCCTCC ACCTGAGCTC     1680

AGACTGATTT TCATTTATGC TTTCTGGTCT TGATAATGCA TTATTAATAT GCTGATTTTG     1740

TCACAATGTC TTAGGATATC TAGTATTATC ACCAAGGATT ACTATATTTC ATGTTATATT     1800

TCATATCTGC TTCAAACACT GGATTTAAAA TAAATATTCC TTTGGTGCAG CAATATCTTT     1860

ATGTTGTTGT ATGTGGTGTA GGTGGGGGTG ATAAAGGCTG TTTTTTTGAA CTTTCTTGAG     1920

GAATTTTTAA TGTAGGACAC TGGAAAGAGT TTCCATTGGC AACTGATTTA CCATGTTCCA     1980

ATGGTTCTTT CATTTTGGAT AAAAAG                                         2006

(2) INFORMATION FOR SEQ ID NO: 12:

(i) SEQUENCE CHARACTERISTICS:
        (A) LENGTH: 1795 base pairs
        (B) TYPE: nucleic acid
        (C) STRANDEDNESS: double
        (D) TOPOLOGY: linear (ii) MOLECULE TYPE: cDNA to mRNA (iv) ANTI-SENSE: NO (vi) ORIGINAL SOURCE:
        (A) ORGANISM: soybean (Glycine max)

(xi) SEQUENCE DESCRIPTION: SEQ ID NO: 12:

TGAGACTGAG GTTGGGTTTG GAAGGCAAGG GCTTGTGTTG TCACAATCCA AGAGAGAAGT       60

AATGGCGAAC ATAGACATCG AAGGGATCTT GAAGCAGCAG CAGCCTTATG ATGGGCGCGT      120

TCCGAAGACG AAGATAGTGT GTACTTTGGG CCCTGCTTCT CGATCCGTAG AAATGACCGA      180

GAAGCTTCTG AGGGCAGGGA TGAACGTTGC TCGTTTCAAT TTCTCTCATG GCACCCACGA      240

CTATCACCAG GAAACCCTCA ACAATCTCAA GACTGCCATG CACAACACTG GCATACTCTG      300

TGCCGTCATG CTTGACACTA AGGGACCTGA GATTCGGACT GGTTTTCTGA AGATGGAAA      360

ACCTATTCAA CTTAAAGAAG GGCAAGAAGT CACCATAACT ACTGATTATG ACATTAAGGG      420

GGATCCGGAG ATGATATCCA TGAGTTACAA GAAGCTGCCT GTCCACTTGA AGCCTGGAAA      480

TACCATACTG TGCTCTGACG GGACGATTAC TCTCACTGTC TTGTCTTGTG ACCCTGATGC      540

TGGTACTGTT AGATGTCGTT GTGAAAACAC TGCAACGTTG GGTGAGAGAA AAAATGTTAA      600

CCTTCCTGGT GTTGTGGTGG ATCTACCCAC ACTTACTGAG AAGGATAAGG AAGACATTCT      660
```

```
TGGATGGGGT GTACCCAACA AGATTGACAT GATTGCTCTT TCATTTGTTC GTAAAGGCTC      720

GGATCTTGTT AATGTCCGCA AGGTTCTGGG GCCACATGCA AAGAATATTC AGTTGATGTC      780

AAAGGTTGAG AATCAGGAGG GAGTCCTGAA TTTTGACGAA ATCCTGCGGG AGACTGATGC      840

ATTCATGGTG GCACGTGGTG ATCTTGGAAT GGAGATCCCA GTAGAAAAGA TTTTCCTGGC      900

ACAGAAGATG ATGATATACA AGTGTAATCT TGTTGGGAAG CCAGTGGTGA CTGCTACCCA      960

AATGCTTGAA TCAATGATAA AGTCTCCCAG GCCAACCCGA GCTGAAGCAA CTGATGTAGC     1020

TAATGCAGTT CTTGATGGAA CAGATTGTGT GATGCTTAGT GGTGAAAGTG CTGCTGGGGC     1080

ATACCCAGAA CTTGCTGTGA AAATCATGGC TCGCATTTGC ATTGAAGCAG AATCATCCCT     1140

TGACTATGGT GCCATCTTCA AAGAGATGAT AAGGTCTACC CCATTGCCTA TGAGTCCATT     1200

GGAGAGCCTT GCATCATCTG CTGTCCGCAC AGCAAACAAG GCCAAAGCAA AACTCATTGT     1260

TGTGCTGACA CGTGGCGGGT CTACAGCCAA GTTAGTTGCC AAGTATAGGC CAGCGGTTCC     1320

AATATTGTCG GTGGTGGTTC CAGTGTTGAG CACGGACTCA TTTGATTGGA CCTGCAGTGA     1380

TGAGACGCCA GCAAGGCACA GCCTGATATA CAGGGGCTTG ATTCCTATAC TGGGCGAGGG     1440

ATCTGCAAAG GCTACCGATG CAGAATCCAC AGAGGTCATT CTCGAAGCTG CTCTTAAGTC     1500

CGCAACAGAA AGGGCCCTTT GTAAGCCTGG TGATGCAGTT GTTGCCCTGC ATCGTATTGG     1560

AGCTGCCTCT GTCATAAAGA TCTGCATAGT CAAATAATGC ATGCTCAACT CAACGTGCCG     1620

CCAACTAATG CAGGGTTATG TTTTGCCTTT TATTTCTTTC TTTCTGCTGT TTATCCGTAT     1680

CATAAAATGG AGGATTTAGT TACTAGCTGT AGATCGAGTG TTTTTTGGTA TACTCTGTTT     1740

ATATTGCGGA GTACTTCTAA ATCAGATTAT CATGGAAATA ATACTCTTAC CTTTT          1795

(2) INFORMATION FOR SEQ ID NO: 13:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: cDNA to mRNA (iv) ANTI-SENSE: NO (vi) ORIGINAL SOURCE:
        (A) ORGANISM: rice (Oryza sativa)

(xi) SEQUENCE DESCRIPTION: SEQ ID NO: 13:

GTCGTTTGTC CGTAAAGGAT CAGATTTGGT TACCGTCAGA CAACTTCTTG GACAGCATGC       60

AAAGCGCATC AAGCTGATGT NAAAGGTTGA ATACCAAGAG GGTGTTNGTA AACTTCGCTG      120

NGATCTTGAG GGNAACGNCT GCATTTATGG TTGCTAGAGG TGATCTTGGT ATGGAGATTC      180

CANTTGAGAN GATATNTCTC GCACAGAAGA TACTNATTTA CAAGTGNAAC CNTTCCGGAA      240

(2) INFORMATION FOR SEQ ID NO: 14:

(i) SEQUENCE CHARACTERISTICS:
        (A) LENGTH: 13011 base pairs
        (B) TYPE: nucleic acid
        (C) STRANDEDNESS: double
        (D) TOPOLOGY: linear (ii) MOLECULE TYPE: DNA (genomic)

(iv) ANTI-SENSE: NO (vi) ORIGINAL SOURCE:
        (A) ORGANISM: rat (Rattus norvegicus)
```

(ix) FEATURE:
    (A) NAME/KEY: CDS
    (B) LOCATION: join(3212..3218, 3766..3948, 5917..6008,
        6152..6283, 6418..6604, 6921..7191, 7302..7452, 7665..
        7817, 7911..8077, 9298..9479, 10163..10269)

(ix) FEATURE:
    (A) NAME/KEY: exon
    (B) LOCATION: join(3194..3218, 3766..3948, 5917..6008,
        6152..6283, 6418..6604, 6921..7191, 7302..7452, 7665..
        7817, 7911..8077, 9298..9479, 10163..11594)

(ix) FEATURE:
    (A) NAME/KEY: intron
    (B) LOCATION: join(3219..3765, 3949..5916, 6009..6151,
        6284..6417, 6605..6920, 7191..7301, 7453..7664, 7818..
        7910, 8078..9297, 9480..10162)

(xi) SEQUENCE DESCRIPTION: SEQ ID NO: 14:

```
GAATTCCAGG GCATCAGCCA AGGATAACCC CAGTGAGCTC ATTACCCCAA AAAGTTGGGC    60
ATCAGGGTAG TTCCAAGAAT CTGGATAGAG AGTGTCCTCT GGTAGGAGCA TGTGCTCAGC   120
TTACTCCTCA CCCAGTCTCC CACGGGTGCT ATTCCCCACT GACCAAACTC TGTGGAAGCC   180
CTGGGACAAA GCCTTTGGCT CCTTGCCCCA AATCAGAGAA GAAGGGGCCA GAGACAGGGT   240
CTGGAGTGAC CCCAGATGCA TGGCACACTC TCCTCAACTC CCTGGGGCCT CCTGTCAGGA   300
CAGGAAAGCA AAAGCATGCC CAGCTGTCAG TCCTGGATTT AATGATTAA CTGGCACTTC    360
AAACACAGCC TGTGCCAAAC AGGAGTCTTG GATTCCACCA TCTTTTTTCT TTCTTTCTTT   420
TCTTTCTTTC TTTTTTTTTT TTGATATTTT TATTTACATT TCAAATGTTA TTCCCTTCCC   480
CGGTTTCCCT TTCTATGAGG ATGTTCCCCC TCCCCAACCA CCCCCCATTC CTGCCTCTCT   540
CTCTCTCTCT CTCTCTCTCT CACACACACA CACACACACA CACACACACA CACACACACA   600
CTCCTCTGTA CTGGGGGTGG GGTGTGGGTG TCCAGCCTTG GCAGGACCAA GGGCTTCCCA   660
TTGGTGCCCA ACAAAGCTGT CCTCTGCTAC ATATGCAGCT GAAGCCATGG GTCTGTCCAT   720
GTGTACTCTT TGGGTAGTGG TTTAGTCCCT GGAGCTCTGG TTGGTTGGCA TTGTTGTTCA   780
TATGGGGTCT CAAGCCCCTT CAGCTCCTTC AATCCTTTCT CTAAAGGGTT CCACCATCTT   840
AACCCTACTT CCACACTTAC CTCAGTGAAC AACAGACACT TCTCCCCTCC CGCCTGCTTG   900
GGTTATATCA GGGCCCCTTG AAAAGCCCTC TGTGCCTTTT CTCCCTACAG CTCCTCCCTA   960
ATTCTTTGGC TCAAGAGAAG GCCCACCTTG ACCTGGTTGG CCTTTGTGAC TATTGTGGGA  1020
GGTCAGAATC CACTGGAGAC CTCACCCAGT CCGAAGCCTT ATGTCTCACC TCCCCAGGAA  1080
AGCCCTTTGC TCCCCTATCC CAGGAATACA GGGTGTTAGC TATCACATCT TCAAAGGTTG  1140
GCTTCAGAGA AAGATGACTT CCTCCTGCTT GCAGTACCTC AGCACTGGCA GATGGATGGG  1200
ACATTTGACC CCAGAGCAAA ACCAGACTTC TCCATGTTGT ACTCCAAGCA CTGAAAGCCT  1260
CCCTTACCAG TACAGCTCCT CATTCCACTC TGCCTTCCCT TTTCCAAAAC ACATCTCACA  1320
GACTTCTCCC TCCCCACAGT GCCACCCAGG CTAGCCTGTC ACCTCCCACC CTGAGCAACT  1380
CCCAAGACTC ACCTGTGTCT CCCTAATCCA CCACTGACTC CACCACTGAC TCCAGCCAGA  1440
GCAACCGTAA ACTTTACTTG AATTATGTCC CTGGCAGCAA TGCCAGTTGC CGCTCAGTGC  1500
CCAGCTTTAC CATGGCCACG TTCTCCCTCC CAGCTTCTTC TACACGGAAA GGTTTTTCTT  1560
CCTCAGAGTT GTGGGATATA TTTAACCTGC AGAGGAATGT GTGTGTGTGT GTGTGTGTGT  1620
GTGTGTGTGT GTGTGTGTGT GTGTGTTTCC TCTGCCCCTG CTGGTCCCCT CTCATCTTTA  1680
ATAGTGTAGG CAGAATCACA TCAAAGAGAG CCGCATCTTC ATTAGGAGGT ACCTAAGACA  1740
CATCACTGCA ACGCCCGGCC CCTCTACCCA GTACCGAGAT CCATCCCTGA CAGCCCCTGC  1800
```

```
CCTGTTTATA GCATTTATTT ATTTGCTAGT AGTCTGTCCC CCACCCCTGC TATACTATAA    1860

TCCACAGACG GGAAAGTTTC CATCTGCCTG ACTCCCACTG TATCCTCAAG GTCTGTCACT    1920

GGCCGGTGTC ATAGTGAGAA TGCCACGGAA GGCCTCCCAG AGAACCCCCC TGTTTTATCA    1980

ACTTTGCGGA ACATGCAAAA CCACCTAAGA CTGGAGTCAG GAGGATCCCC AGAGTAGGGC    2040

CTTCTGGGAT TCAAGAGAGC AGTAAGTGCC AGGTGGTCCC CTTGGTAGTG ATAGGGGATT    2100

CTGCCTGCAG GACTGCAGTT TACCATCATG GTGGTCAACA AGGCAAGGTC ATTCTCCCTG    2160

GTGCTATGGT ATGATCTCCC TGGTGAGATC GATGCCCTTG TGATGGCTGA GGAGATCCCC    2220

TGTACTCAGG TTTCCATGTG TTTATCCATA CGGCTGGTCA ACAACAATAC AAGTTTATGA    2280

GTTAGTGCCT AGGAATGTTC ATGGTTTCAT CTCTGGGTTC TCAGAGGAAC ATGTGCGAGA    2340

AACTGAGAGA CCCTCTAACC TTTAACTACC AAAGGGTATC CCTGTTTTCC ACAGCCTAGT    2400

CCCCACCTTC AAGCTCTTGT TCTGAGAATA CACCTAAGAT TCTCTTCAAT AAAATGCAAA    2460

GAGAAAGGCA TTGTACTGTT GGCAATCAAC CAATCTCTTC TCTAATGATG AGCCAACAAT    2520

GTGAATGGAC TAATGATTGA TCAGGAAAAA ATAGATGACC TAGGGAAGG GGAGAGATGG    2580

GGGCCCCACA ACAGGCAGTC CTTGAGAAGG GACTCTGTGG GGATGGGGCT GCCTGCTGGG    2640

TGTGCCCCTT TTCTATTCTC TGGCTTCCTC AGATAAGACC AGCAGTTAGG GTACACTCTC    2700

CTCCCAGTCT GCCGTTCTTG CAGACACAGT TCCACGCTTT GGAAGCATGT CTGTCCAGGA    2760

GAACACTCTA CCCCAGCAGC TCTGGCCGTG GATCTTTAGG TCCCAAAAAG ACTTGGCAAA    2820

GTCTGCCTTA AGTGGGCTC CCGGAGGTAA GAAGAGGAAG GGAAGCCACT GAAGAGAGAG    2880

GAGAATTAGG GTAGAATCAG CGTTGAGAGA TGGAGGCCTT GTGGGGTAGG ATGCCCAATA    2940

TAGCCTCACC TCGGCTAAAT ACAGACCTGA TCTGAGCCTT TGATCCAGGC TCTGCAGACA    3000

GGCCAAAGGG GATCCAGCAG CATGGGCGCA CGGGGCACTC CCGTGGTTCC TGGACTCTGG    3060

CCCCCAGTGT ACAAGGCTTC CGTTGGCAAG AGAGATGCTA GCTGGTTATA CTTTAACCAG    3120

GACTCATCTC ATCTGAGCCA GGCCCCATCC CACTGACAAA GGCGCAGTAT AAAGCAGACC    3180

CACAGACACA GCAGGTAAGC AACGTAGCAG CATGGAAGGT GCTTCTAAAC CGGGTGCTCT    3240

ACTGAGCAGG GCTGGGTCAA GCTACGGATC CAGCGCAGCC TTGAATGGGT GGAGGGAAGG    3300

TGGAGGGGAG GGGAGTGGAG AAGGCCAGAG AATTGCCTGG AGCTGGAAGA AGTAAACAAG    3360

AAAATGAGGG AAAGTAAGCT GAGTGTTTGC AGGCCTAGAT AATGAGGTGC AGGCTTGAAG    3420

GAGGCCTCTG GGAGGGCTGA AGCTGAGTGG TCTGCAGCGG TGTGACGCTT GGGGAAGGTC    3480

TCTGTAGCTT GGGGATAGAC CTGGATTTGA ATCATCTCAC TTGGCTGATG CATTTTTTTT    3540

TTCTTAGACA ATGTATTTTT TTTTCCCCTT GGTCTTTTTC TTACTTGTAA AGTGGGGATA    3600

GAGCAGGACC CTGGAGACTA AACAAAGTAG CGGGTGTGTG ATAGTCAAAT GGGAGGAAGA    3660

CCTCGCACCA TCTGGAGATC TGAATAGACA CAGGGTGCAC TGGCAGGAAG CACATGGGGG    3720

ACAGGCAGGT GTCTGTGCAA GAGCCTGAGT TTCCATCTAC GGCAGGGCCA GCGGGATACC    3780

TTCGACGTGC GAGTGTGGCT CAACTGACCC AGGAGCTGGG CACTGCCTTC TTCCAGCAGC    3840

AGCAACTGCC GGCAGCTATG GCGGACACCT TCCTGGAACA CCTCTGCCTT CTGGATATCG    3900

ACTCACAGCC TGTGGCTGCT CGTAGCACCA GCATCATTGC CACCATTGGT AAGACCACCC    3960

AAGCCCTAGA AGCCACACAG GGCCACCCAC ATGGCTCAGG TGTCTCCTTA CTTTGCTATC    4020

CTTGTTGTGG TCATTCATTC AACAAATATT TGTGAGATTT GTGCAGGGGT AGGGGGTGGG    4080

TTTGTTTTTG TTTTTGTTTT TGTTTTTTTG AGATCGGGTC TTTTTATGTT GTAGCTCTGA    4140

CTGATGGATA GGCAGGTCTC AAATTTAGAA ATCTCCCTAC CTTTGCCTCC TGAGAGTTGG    4200
```

```
ACTGGGACCA CCTTGCTCCA CATGAGGCTG GGTTTTTGAG ACAGGGTCTC AGGTAGCCTT    4260

GGATATTTCT AGCTTATTTC ATAGACCCTA TTATATCGTC TTAGCCTGGT GAAAGCATAG    4320

GTATGTGATA CCACACCCAA CTTAACAAAT GCTTGTTGAG TACCTGGAAA ACAAGGTTTG    4380

GAATTGGGGG GTAGACTCTA TCTCAAAAAC AAATAAGAAC GAGGAAAGGT GTCATCTGCA    4440

CACAGATGGC CTTCCAAGGA TAAGGACGGC TGGGATCACA GAGAAGTGAA AGGTATATAT    4500

AATGAACTGA GGACCAGACA GACACACACC TAATACACAC ATGTCACACA ACATACACAC    4560

ACACCACACA CATACACATG CACCACACAC ATACACACAC ACACCACACA TATACTACAT    4620

ACCCACACAC ACACCACTCA CATATCACAC ACATGTACCA CACATACACA CATCTTGCAC    4680

ACACACACAC ACCACACACA TATCACTCAC ACATCACATA CATATACCAC ATATACACAC    4740

AGCACACACA TACACCGTAT ATGCACCATA TCACATACAC ACACCATT CACACGTCAC      4800

ACACACACAT GCACTATACA CACACACCAC ACATAACACT ACTCACACAT GACACACATA    4860

TACTACACAT ACACAAATCA CTCACACATA CCATTCATAC ACATACATCA TACACACATA    4920

CCACACACCA CTCACATATA CACCACACAC ACAAACATGT ACAGGCCACA CACACACACA    4980

CACACACACA CACACACACA CACACACACA CACCAGTCCT CACACATTAT GGCTCAGCAT    5040

GCTCAGCAGA TAAAGTCTTG TCATGGAGCT GGGTGACCTG AGTTCAATCC CTGAAACCAC    5100

ATGGAGGATT CGGCCACACA CACCAAAAAC AAAAACAGAA CTCAGTCCAG CCAGGCTATG    5160

AGGCCCTGTT TCAAGGAGAG AGGGTGGGCA GTAGCTCTGT TGTTAGAACA CTTGCCTCCT    5220

GCATGAAGCC CTGGGTCCGT CCTAGCGCTA CATAAATTGG CTGTCGTAGA GTACACCCTT    5280

AACCCAGCAC AGGGGAGGAC AGGAGAACCA AGCCCAAGGT TATCCCCAGA AGCCAGAGCA    5340

AACCCAAGGC TAGCCTGGGT TATGGGAGTC CTTGTCTCAG AAGGAAGGAC TGTTATTCCT    5400

AAAGAATGGG AGATAAGGAT GGGTGTAGCT CAGTACTATA GCATTTATTT GCCTCGCATG    5460

TAGAAGGCCC TGGCCTCCAT CTCCAGAGCA GAAAAAAAAA ATGGTGGCCA GGGAAGAAGA    5520

GGGAGGGGGA AGTGCATACA GCGAGCTGCT GCTGCTGCTG CAGGCTGACG TGGATGAAGA    5580

CAGGGACAGA TCTCAGTTCT GTCAGTGAGA TTGCTCAGCT TTCAAAGTGC CTTTTTGACC    5640

TGCCTGGCGT TCTGACCCTT CACAGCCTAC AGTAACCTCC ACAGCATACA CTTATGTCAG    5700

GTCACTTGCT AACAAAGGTC CTGAGGCCTG ACTGAGATTT AGACATTCCA CAAGCTGCCT    5760

TCCCAAGGGC TGTGTACTGG TTGGAGTGGG GGAAAAAAAG AGTTTGTGAG TAGAGGAACT    5820

TCGAAGGACT CCTGGGTAGG GGAGTCTCTC CGATGTTGCA GATGGGTTTG ACTGTCAGGC    5880

TTGGGAGGAC CTTCTTAGTG GGTTCTCTGG TTCCAGGGCC AGCATCCCGC TCTGTGGACC    5940

GCCTCAAGGA GATGATCAAA GCAGGGATGA ACATTGCACG ACTCAACTTC TCCCATGGCT    6000

CCCATGAGGT GTGGGAAGA AGTCATGGAG GGTGGAGCTG AGAATGCCCC CAAGGTCCTG     6060

TTCACTTTGC CTTAAGATCC AGGTTTTGTT CTCTCTCTCT CTCTCTCTCT CTCTCTCTCT    6120

CTCTCTCTCT CTCTCGCTTT CTCTCTGGTA GTACCATGCA GAATCCATCG CCAACATCCG    6180

GGAGGCAACT GAGAGTTTTG CAACCTCCCC ACTCAGCTAC AGACCTGTGG CCATCGCCCT    6240

GGACACCAAG GGACCTGAGA TACGAACCGG AGTCTTGCAG GGGGTGAGAA GCCTTTGGGT    6300

CCGAGCTGTC TGGGGCCTGG AGGAGCATGA GAGCCCTGGA GCAAGAGAGA GGGTCCCTAC    6360

CCTCTCAGGG TCCACTTGCA AAACTCAGGC TTCTCTACCC ACCCCACTCC CCTCCAGGGT    6420

CCGGAGTCGG AGGTGGAAAT TGTGAAGGGC TCACAGGTGC TGGTGACGGT GGACCCGAAG    6480

TTCCAGACAA GGGGTGATGC AAAGACAGTG TGGGTGGACT ACCACAATAT CACCCGGGTC    6540

GTTGCAGTGG GGGGCCGCAT CTACATTGAC GACGGGCTCA TCTCCTTAGT GGTACAGAAA    6600
```

```
ATCGGTACAG AAATGCATCC TGATCTTATG AGGCGCTCCC AAAACCCTGA ACAGGGCAT    6660

TTTCTCTTCC CTTTGGTTTC TATGTTCTGT CAGCTCCTTA CCCATACCTT CCCCTAGTGG    6720

TGCTTGCTTC TCCACCTGTC CTAGTGGTCC CTGCTGTCAT CATGGGTTGG AGCTGAGCAT    6780

TTGATGCCTC TTCTTGTGTG TGGAGTGAGT GAAGGGTTCA GAAGATTCCA ATTTCTGGAG    6840

GATCCAAGCT TAAGAGTTCC CTCTGCAGTG CCTATATCGC AGCTCAGCCT TACAGACACT    6900

GGTTCTCTCT ATACCCGCAG GCCCAGAGGG ACTGGTGACA GAAGTGGAGC ACGGTGGTAT    6960

CTTGGGCAGC AGGAAGGGTG TGAACTTGCC AAACACTGAG GTGGACCTGC CCGGGCTGTC    7020

TGAGCAAGAC CTTTTGGATC TGCGCTTCGG GGTGCAGCAT AATGTGGACA TCATCTTTGC    7080

CTCCTTTGTG CGGAAAGCCA GTGACGTGTT AGCAGTCCGG GATGCCCTGG GGCCAGAAGG    7140

ACAGAACATC AAAATTATCA GCAAAATCGA GAACCATGAA GGCGTGAAGA AGTGAGGCTT    7200

AGTCTTTGGT CCGTCAGCCC TCTGTTTCTC TTTCCCTCTC TTCTGCATGA TATTTCCTGC    7260

CATCTCCTCC TCTGCCTAGC CTGGATTCCT CCAACCACCA GGTTTGATGA AATTCTAGAA    7320

GTGAGCGATG GCATCATGGT GGCACGGGGT GACCTGGGCA TTGAGATCCC TGCGGAGAAG    7380

GTTTTCTTGG CTCAGAAGAT GATGATTGGA CGCTGCAACC TGGCCGGCAA GCCTGTCGTT    7440

TGTGCCACAC AGGTCTGGAG CAAACCCTTG GGCTTTAAAG GTGCTGAGAA ACCTACATGT    7500

TGCTGTCTGG TGCCTGGTCA CAAAAGACGA TGACATGAAC TTCCAGGGTC TTACTGTGAC    7560

CCTGGCACTC TAAGCGTGCA GGTGCCAGAG AAATAGCGTG GGCGGGTTCG GGTCCCCAGT    7620

CAGAATGTGA CTTCTACAGC TTTGACATCC ATGGTGTCAC TCAGATGCTG GAGAGCATGA    7680

TCACTAAGGC TCGACCAACT CGGGCGGAGA CAAGCGATGT GGCCAATGCC GTGCTGGATG    7740

GGGCTGACTG TATCATGCTG TCCGGAGAGA CCGCCAAGGG CAGTTTTCCT GTGGAAGCTG    7800

TAATGATGCA ACATGCGGTA GGTACTCCGT TCTGAAAAGC TGCTGGGCCA GCGACACAGA    7860

CCCCTCTGGA ACCCCGTTGA CTACTCAACC TGACCTACTG GTCCCTGCAG ATTGCGCGGG    7920

AGGCAGAGGC CGCTGTGTAC CACCGCCAGT TGTTTGAGGA GCTACGCCGG GCAGCGCCGC    7980

TGAGCCGTGA CCCAACTGAG GTCACTGCGA TTGGAGCCGT GGAGGCTTCC TTCAAGTGCT    8040

GTGCAGCAGC CATCATCGTG CTGACGAAGA CTGGCCGGTG AGAAACATAT TGGAAACAGG    8100

GCTTTGGGCA GGGGCGGCTG ACACAGAGGC TAATAAAAAA AGCACTGCTT TAGGGCAAGC    8160

AAAGAAACAG CCATGGATGC TAGAGGCCAG GAGAGGCTAG AGGCTTGGAC AGGTGGCTTT    8220

TTGATGATCT AGAATCAGAG CCAGTGATGG GGGGGGGGGG GCGCACGGGG ACGGGGACGC    8280

AGCAGGTGAT AACCCAAGCA CGTTGGCCTT AGGGTATTTG AAGACCAGGC TCTGACAGAT    8340

CTTCACTGTG CTGAGGTGTT GCTGAAAAAC CCAGTAGGCC CAAGAGCTGA GGATTTTCT    8400

CAAACTTAGT AGTGAGATCC TAAGTAATTG TTAGGGCTTA CAAGCCTTGA CTCCATGGAT    8460

CTGTGTGAGT TTTTCATTTG TCCCCACCCC ACCCCACCCC CATGGGGTTG TGAGGATTAA    8520

CAAAAAATGG TTAAGAGTCA TATGGAGGTT GGGAATGATG TAAACATATC TTCTAGACAG    8580

TTTTACCCTT TTTTTGTTGT TTGTTTGGTA GGATTTTTCT GACATAGGGA CTTATTAGTC    8640

CTGGCTGGCC TGAAACTTCC TTAGTACCTG AAGTAGCCTT GAACTTAACC CTTTACCCCG    8700

AGGGCTGAGG TTGTGGGCGT GTCTCACCAC GCCTGGCTGG CTTTACATTT CTAATTTTTT    8760

GGAGGATTTA TTACTTTTAT GTGTGCATGT ACAGTTCTAA GGCGAGAAGA GGTTGGACCC    8820

TCTGGAGCTG GAGTTACAGG CAGTTGTAAG GGATTTGATG TGGGTGCTCA GAACCAACTC    8880

TGGTCCTCAG AAAGAGCAGT GCGAGCCTTT AAGAACTGAG CCATCTCTCT AGCCCAGGTT    8940

TTACATTTAT CTTTCAATAT GGATTGACAT TTTGCCTGCC CTTACGTCTG AGCACCATTT    9000
```

```
GCATGTCTGG TGCCAGTGAA GGCCAGAAGA GGATGTTAGA GCCCCTGAAA CTGGACTTAA      9060

AAACCATTGT TAGCCACCAT GCTGGTGTTG AAAACGTAAT CCCAGCGTGT GCTCTTAATG      9120

GTGAGCCGTC TCTACATCAG GGTAGGTCTT CTTACTACTT AATGAGAAAG ACAAAGATCA      9180

GAGGAGTATA CCTTACCCAA GGACACAGGG TTTGTTAGTG ACAGTGACAC CTGGAACCAT      9240

AATTCAAACT CGTTTCTTGG GTCAACACTC AGAGCTAACC TTTTCTTCCT CATGCAGTTC      9300

AGCCCAGCTT CTATCTCAAT ACCGACCTCG GCGGCTGTC ATTGCTGTGA CTCGATCTGC       9360

CCAGGCTGCC CGACAGGTCC ACCTGTCCCG AGGAGTCTTC CCCTTGCTCT ACCGTGAGCC      9420

TCCAGAGGCC ATCTGGGCAG ATGATGTGGA TCGAAGGGTC CAATTTGGCA TTGAAAGTGG      9480

TGAGCCTTGC CCTCTGTTCC ACAGCCTGCC TTCTTACCCC GACTCCAAAG CTCTGTCTGT      9540

CCTCACTGGC CCAAGTTTTC TAGGAATCGC TAAGATGGAC ATGTCTTGGG CTTTATTTTT      9600

GTTTTTTTGT TTGTTTGTTT TTTGTTTTTT TTTTAAAGAT TTATTCATTT ATTATATATA      9660

AGTACACTGT AGCTGTCTTC AGACACACCA GAAGAGGGCA TCAGATTCTG TTACAGATGG      9720

TTGTGAGCCA CCATGTGGTT GCTGGGATTT GAACTCAGGA CCTCTGGAAG AACAGTCAGT      9780

GCTCTTATCC GCTGAGCCAT CTCTCCAGCC CATGTCTTGA GCTTTAAAGC AGGAAGGGTA      9840

GGCTGAGAGG AAAGGAGTGA GAGCAGGACC CCTGAGAAGT CCTTGCTGCT GTCTGCCACA      9900

GCCTAGTAGG ACACATCAGT AAGAGGAGGT TCCAGAAGAG CTGGAACTAA ATTTTAATTT      9960

ATAGTTGTCC TTGTCCCATT AGTGCAGCCA CATGGGTGAA AAGGCTCAAT GCTGAAAAAC     10020

AGTATACAGC ATCCCTCCAC ACACACATCC TCTCAAACCA CTGCCTTTGG TTCCTTTCCC     10080

CTACAGGATA GGTAGCCTTG AGGTGGTCGA TGCTAATGGC TGACCCAGGT TCTTCAATGA     10140

CTGTCATATT TTTCTCCACC AGGAAAGCTC CGTGGTTTCC TCCGTGTGGG TGATCTGGTG     10200

ATTGTGGTGA CAGGTTGGCG GCCTGGCTCT GGCTATACCA ACATCATGCG GGTGCTGAGC     10260

GTATCCTGAA ATGCCTCTCC CCATTCTGAC CCAGTTACAC CCTATTTCTT TCAACCCACA     10320

CCCCTCCCAT AGTCCTACAT CTGCCATCTA GCCCCATCCC TGTGCTTTAC ACAGCCCTGA     10380

ATGTCTGTGT CCAATTATAC AGTGGCCACC GGCAGCATCG GTTGTATATC CCTGTCTCAA     10440

TCCGCTCAGC TGGACTCTAA GATACCCTGA GCCTTTAATC CCAGCCCAGC TGGTGATTCG     10500

ATTCCTTCCG GGTCCCAATC ATTGGAATGG GGGAGTGGAA ACAGGGTGAT CTTGTCCAAT     10560

TTTCATACAA TCATGATTTT AAAACACTGT CTGATATAAC CCTCATGATC AGTTCCTAGC     10620

AAAGTGTCAT CTCCTAATGG CCTCAAGTCA GGGCAGAATA CTCCTTCAAG GAGCACAGCT     10680

CCACACTTTA GGGAAGGCTG GGGCAGCTGG GTACTGGAGA GAACTAAGAC AGGCGGCTTT     10740

TCTCTCTCTC TCTCTCTCTT TTTTTTTTTC TTTTCTTTTT CTTTTTTTCG GAGCTGGGGA     10800

CCGAACCCAG GGCCTTGTGC TTGCTAGGCA AGCGCTCTAC CACTGAGCTA ATCCCAACC      10860

CCAGCTTTTC TCTTTTTAAT ACAAGCTCTC ACTGGCCTCA AACTCCTAAG TCCTCCTGCC     10920

TGGCCCTCCT AAGGGTAGGG ACTACAGGCA TGAGTGACCA GCTGGACTTC GGGTGCCTTA     10980

TTTTCTTACT GACTCCACAA ACCATGGTTG TTCTCCTGCC CACTGCTCTG CTGGGTCAGA     11040

TGATCCAGAA ATTCTTCCAC AACCACTTGG CTCCCACATA CAAATTAGAA GCAAACTGAA     11100

TCTTTTCTTT TAAACCCAAC TGTTTAGGTG CAATTATAAA AACAACTCCC ACAGGCAAAG     11160

AATCCCAGAA TCTCCTACCC TAGGAGATGT ATAGTCCTGG CCCCACCCAT CAATCTGTAG     11220

TATACTCCTG AAGCGGGACA GAACTGGTGG ACAGGGACT CCTCTTGTCC CTAAGAAAGT      11280

GGAGGCACTG TTGGCCCACC CCTCCTAGGT TTGAATACTC CAGGCCCTCC TCTTAGCACC     11340

AACAGCAAAT CCAGATGAGG AAAAAAAAAT AAGTGCAGTT CTCCTGCTGC CCTCCTCTTT     11400
```

```
TCACTACCTC AATACAGCAA GTTTGAGTAT TGCTGCTGAT GGCAGTGTGC AAGGCCACAA    11460

AGATGTCCCC CCTCAGCCCC CTACCAGAAG GTGGAGAGGA CAGAGGAATG AATAATAAAG    11520

TGAATGCGTC AAATTAGCAA ATGAATAAAT AAAATTAATA AGTGACTGAA TAAGACACAG    11580

GGAAAGATAA AAGGTCACAT GAGGATTCAG CCCCTTACCC CCTACCTGGG GGAGCTAGGC    11640

TAGCACAGTA AGGAGGCGCC AAGTATCCCT TAGCTTTAGG GCAACACCAT TGAGTCAGGG    11700

AGCACAGTGA AGAGCAGCTT CTAGTTTACA AAGGTAGTGC TTTCCACACA GGAGCTGCGG    11760

AGGGCAGACT ACAGTGGGCA GAGATACCCG TTCTCACGTG GTGTAGACAA GGACGGTCCG    11820

TCCACACGTG GCAGTGAGAG GGAAGATGGT CACACCTAGG GCCCTAGACA TCTGTTGGCT    11880

GTACTAGATA ATTGACAGTA CCCAGCTACG ACAATGGGA TGGGAAGAAA GGACACACTG    11940

GGCACAACCT GCAGGGTCAC TGACAGGGAG ACAGCCATCT AGTCACTCGG CAGTGAAGGA    12000

AGCAGCAAGT ACTTGTGCTT AATAAAGGCA GGGCTGTGGG CCCAAGCCTG CACCTGGCAG    12060

GACTGTGGCC TGGGACACAC TTGTTAAAGG GCTTTGAGTC ACTTCTACTT GGCAGTGGCT    12120

ACACATTGTA CTTAGCACAA TGCCTTGACG GGTAGGCAC TGGTACCTAT GACAAATGGG    12180

TATGTGATTA GGATTCGCAG GCTGCAGCTG CTATGAGCTG AGGACACAGA GGACAACTTT    12240

GTGGTAGTAA AGGGCAGTGT GTTAGATCCC CGCAGCCTTC CCCAGGGGCG TCTACCCTCA    12300

GGCACACCTT ATTGCGTGCC AATAGCTAAG GCCAGTGCAA TCTAGGATTT CACATGTTGG    12360

CAGAAATTTG GGGACCTCTG GGGGTAACTG GCTCAGGCAC TGATGACCTG GATGGCTGGA    12420

CAGTCCCTGG AGGCTTGGCC AGGAGCCCCA AGGGCAGCAC GCTCACTTCC AGAGCCTTTG    12480

CGCCTAGGAG AGCCATCCCC CGTGGCTCGC TGAGGCAGAG AGGGTTGAGA GGCAGAGAGT    12540

GGGCGGCCCC TAGGTCCTAG CCTCCGACCA CCTCCTCCTG GGGAGGGCCC AACAGAGACA    12600

CCTGGGAACG CCCTGTCCGG GATAGGCTGG CATGGAGGGT TCGGGCAGGT GGAGGGGAG    12660

GGCCCAACAG AGACACCTTG GGAACCCCTG TCCGGGATAG GCTGGCATGG AGGGTTCGGG    12720

CAGGTGGAGC AGGCAGGCGA GAAGTGGACG CCCAGGGTCC CCGGGCCAGC AGAGGACCTG    12780

CTCGGACAGG CACCAGTGGG GAGGCTGGGG AGCCTGCTGA GCGTCTAGCA GATCGAGCCA    12840

GGAGGGTGGC TGGAGAATCA GGGGAGAGGG GCAGAGGGCC TCGCTGATGA GTCAAGGCTA    12900

TGGCCACGTT GGAGGTCACA GCAGCTGCCT GCAGAGGTGC GTGTACCAGT GGTTCCCACA    12960

GCACTGGCTT TCCACTGAGG CGAGCTCCTG TGCCCGGAGC CAGACCCCGA A             13011

(2) INFORMATION FOR SEQ ID NO: 15:

(i) SEQUENCE CHARACTERISTICS:
        (A) LENGTH: 2885 base pairs
        (B) TYPE: nucleic acid
        (C) STRANDEDNESS: double
        (D) TOPOLOGY: linear (ii) MOLECULE TYPE: DNA (genomic)

(iv) ANTI-SENSE: NO (vi) ORIGINAL SOURCE:
         (A) ORGANISM: Saccharomyces cerevisiae (xi) SEQUENCE DESCRIPTION: SEQ ID NO: 15:

GATCCAAATG TAAATAAACA ATCACAAGGA AAAAAAAAA AAAAAAAAA ATAGCCGCCA      60

TGACCCCGGA TCGTCGGCTT GTGATACGGT CAGGGTAGCG CCCTGGTCAA ACTTCAGAAC   120

TAAAAAAATA ACTAAGGAAG AAAAAAATAG CTAATTTTTC CGGCAGAAAG ATTTTCGCTA   180

CCCGAAAGTT TTTCCGGCAA GCTAAATGGA AAAAGGAAAG ATTATTGAAA GAGAAAGAAA   240
```

```
GAAAAAAAAA AAATGTACAC CCAGACATCG GGCTTCCATA ATTTCGGCTC TATTGTTTTC    300

CATCTCTCGC AACGGCGGGA TTCCTCTATG GCGTGTGATG TCTGTATCTG TTACTTAATC    360

CAGAAACTGG CACTTGACCC AACTCTGCCA CGTGGGTCGT TTTGCCATCG ACAGATTGGG    420

AGATTTTCAT AGTAGAATTC AGCATGATAG CTACGTAAAT GTGTTCCGCA CCGTCACAAA    480

GTGTTTTCTA CTGTTCTTTC TTCTTTCGTT CATTCAGTTG AGTTGAGTGA GTGCTTTGTT    540

CAATGGATCT TAGCTAAAAT GCATATTTTT TCTCTTGGTA AATGAATGCT TGTGATGTCT    600

TCCAAGTGAT TTCCTTTCCT TCCCATATGA TGCTAGGTAC CTTTAGTGTC TTCCTAAAAA    660

AAAAAAAAGG CTCGCCACTC AAAACGATAT TCGTTGGCTT TTTTTTCTGA ATTATAAATA    720

CTCTTTGGTA ACTTTTCATT TCCAAGAACC TCTTTTTTCC AGTTATATCA TGGTCCCCTT    780

TCAAAGTTAT TCTCTACTCT TTTTCATATT CATTCTTTTT CATCCTTTGG TTTTTTATTC    840

TTAACTTGTT TATTATTCTC TCTTGTTTCT ATTTACAAGA CACCAATCAA AACAAATAAA    900

ACATCATCAC AATGTCTAGA TTAGAAAGAT TGACCTCATT AAACGTTGTT GCTGGTTCTG    960

ACTTGAGAAG AACCTCCATC ATTGGTACCA TCGGTCCAAA GACCAACAAC CCAGAAACCT   1020

TGGTTGCTTT GAGAAAGGCT GGTTTGAACA TTGTCCGTAT GAACTTCTCT CACGGTTCTT   1080

ACGAATACCA CAAGTCTGTC ATTGACAACG CCAGAAAGTC CGAAGAATTG TACCCAGGTA   1140

GACCATTGGC CATTGCTTTG GACACCAAGG GTCCAGAAAT CAGAACTGGT ACCACCACCA   1200

ACGATGTTGA CTACCCAATC CCACCAAACC ACGAAATGAT CTTCACCACC GATGACAAGT   1260

ACGCTAAGGC TTGTGACGAC AAGATCATGT ACGTTGACTA CAAGAACATC ACCAAGGTCA   1320

TCTCCGCTGG TAGAATCATC TACGTTGATG ATGGTGTTTT GTCTTTCCAA GTTTTGGAAG   1380

TCGTTGACGA CAAGACTTTG AAGGTCAAGG CTTTGAACGC CGGTAAGATC TGTTCCCACA   1440

AGGGTGTCAA CTTACCAGGT ACCGATGTCG ATTTGCCAGC TTTGTCTGAA AAGGACAAGG   1500

AAGATTTGAG ATTCGGTGTC AAGAACGGTG TCCACATGGT CTTCGCTTCT TTCATCAGAA   1560

CCGCCAACGA TGTTTTGACC ATCAGAGAAG TCTTGGGTGA ACAAGGTAAG GACGTCAAGA   1620

TCATTGTCAA GATTGAAAAC CAACAAGGTG TTAACAACTT CGACGAAATC TTGAAGGTCA   1680

CTGACGGTGT TATGGTTGCC AGAGGTGACT TGGGTATTGA AATCCCAGCC CCAGAAGTCT   1740

TGGCTGTCCA AAAGAAATTG ATTGCTAAGT CTAACTTGGC TGGTAAGCCA GTTATCTGTG   1800

CTACCCAAAT GTTGGAATCC ATGACTTACA ACCCAAGACC AACCAGAGCT GAAGTTTCCG   1860

ATGTCGGTAA CGCTATCTTG GATGGTGCTG ACTGTGTTAT GTTGTCTGGT GAAACCGCCA   1920

AGGGTAACTA CCCAATCAAC GCCGTTACCA CTATGGCTGA AACCGCTGTC ATTGCTGAAC   1980

AAGCTATCGC TTACTTGCCA AACTACGATG ACATGAGAAA CTGTACTCCA AAGCCAACCT   2040

CCACCACCGA AACGTCGCTG CCTCGTGTCG CTGCTGTTTT CGAACAAAAG GCCAAGGCTA   2100

TCATTGTCTT GTCCACTTCC GGTACCACCC CAAGATTGGT TTCCAAGTAC AGACCAAACT   2160

GTCCAATCAT CTTGGTTACC AGATGCCCAA GAGCTGCTAG ATTCTCTCAC TTGTACAGAG   2220

GTGTCTTCCC ATTCGTTTTC GAAAAGGAAC CTGTCTCTGA CTGGACTGAT GATGTTGAAG   2280

CCCGTATCAA CTTCGGTATT GAAAGGCTA AGGAATTCGG TATCTTGAAG AAGGGTGACA   2340

CTTACGTTTC CATCCAAGGT TTCAAGGCCG GTGCTGGTCA CTCCAACACT TTGCAAGTCT   2400

CTACCGTTTA AAAAAGAAT CATGATTGAA TGAAGATATT ATTTTTTGA ATTATATTTT    2460

TTAAATTTTA TATAAAGACA TGGTTTTTCT TTTCAACTCA AATAAAGATT TATAAGTTAC   2520

TTAAATAACA TACATTTTAT AAGGTATTCT ATAAAAAGAT AACTTATGTT ATTGTTAACC   2580

TTTTTGTCTC CAATTGTCGT CATAACGATG AGGTGTTCGA TTTTTGGAAA CGAGATTGAC   2640
```

```
ATAGAGTCAA AATTTGCTAA ATTTGATCCC TCCCATCGCA AGATAATCTT CCCTCAAGGT    2700

TATCATGATT ATCAGGATGG CGAAAGGATA CGCTAAAAAT TCAATAAAAA ATTCAATATA    2760

ATTTTCGTTT CCCAAGAACT AACTTGGAAG GTTATACATG GGTACATAAA TGCAGATGCC    2820

AGTGAACTAT GTTCAGCTTC TGGCCTTCGT TTGGTGGTTT AATCTATTTT TTATAAAAAA    2880

TGACG                                                                2885
```